US009572666B2

(12) United States Patent
Basude et al.

(10) Patent No.: US 9,572,666 B2
(45) Date of Patent: Feb. 21, 2017

(54) MITRAL VALVE FIXATION DEVICE REMOVAL DEVICES AND METHODS

(71) Applicant: Evalve, Inc., Santa Clara, CA (US)

(72) Inventors: Raghuveer Basude, Fremont, CA (US); Kent Dell, Redwood City, CA (US); Arundhati Kabe, Sunnyvale, CA (US); Gaurav Krishnamurthy, Mountain View, CA (US); Michael F. Wei, Redwood City, CA (US)

(73) Assignee: Evalve, Inc., Santa Clara, CA (US)

( * ) Notice: Subject to any disclaimer, the term of this patent is extended or adjusted under 35 U.S.C. 154(b) by 319 days.

(21) Appl. No.: 14/216,787

(22) Filed: Mar. 17, 2014

(65) Prior Publication Data

US 2015/0257883 A1    Sep. 17, 2015

(51) Int. Cl.
*A61F 2/24* (2006.01)
*A61B 17/064* (2006.01)
*A61B 17/068* (2006.01)
*A61B 17/00* (2006.01)
(Continued)

(52) U.S. Cl.
CPC ......... *A61F 2/2463* (2013.01); *A61B 17/0644* (2013.01); *A61B 17/0682* (2013.01); *A61F 2/2466* (2013.01); *A61B 17/32053* (2013.01); *A61B 2017/00243* (2013.01);
(Continued)

(58) Field of Classification Search
CPC .................. A61F 2/2463; A61F 2/2466; A61F 2250/0071; A61F 2250/0082; A61F 2/2454; A61F 2/2442; A61F 2/2487; A61B 17/0644; A61B 17/0682; A61B 17/32; A61B 17/064; A61B 17/32053; A61B 2017/00783; A61B 2017/22097; A61B 2017/00243; A61B 2017/00867

See application file for complete search history.

(56) References Cited

U.S. PATENT DOCUMENTS

| 3,671,979 A | 6/1972 | Moulopoulos |
|---|---|---|
| 3,874,338 A | 4/1975 | Happel |
| 4,056,854 A | 11/1977 | Boretos et al. |

(Continued)

FOREIGN PATENT DOCUMENTS

| EP | 2641570 | 9/2013 |
|---|---|---|
| WO | WO 91/01689 | 2/1991 |

(Continued)

OTHER PUBLICATIONS

U.S. Appl. No. 14/216,813, filed Mar. 17, 2014, Hernandez.
(Continued)

*Primary Examiner* — Amy R Weisberg
(74) *Attorney, Agent, or Firm* — Workman Nydegger; John Kwok

(57) ABSTRACT

Procedures may be performed on the heart after the installation of a mitral valve fixation device. In order to prepare the heart for such procedures, the fixation device may be removed or disabled in minimally invasive ways (e.g., through an endovascular procedure), without requiring open access to the heart. The fixation device may be partitioned so that one portion may remain attached to each leaflet of the mitral valve. In another example, the leaflets may be cut along the edges of the distal element(s) of the fixation device, so as to cut the fixation device from the leaflet(s). Systems and devices for performing such procedures endovascularly are disclosed. Fixation devices with improved access to a release harness are also disclosed.

6 Claims, 24 Drawing Sheets

(51) Int. Cl.
   *A61B 17/3205* (2006.01)
   *A61B 17/22* (2006.01)
(52) U.S. Cl.
   CPC .............. *A61B 2017/00783* (2013.01); *A61B 2017/00867* (2013.01); *A61B 2017/22097* (2013.01)

(56) References Cited

U.S. PATENT DOCUMENTS

| | | | |
|---|---|---|---|
| 4,484,579 A | 11/1984 | Meno et al. | |
| 4,878,495 A * | 11/1989 | Grayzel | A61M 29/02 604/101.01 |
| 4,917,089 A | 4/1990 | Sideris | |
| 4,994,077 A | 2/1991 | Dobben | |
| 5,332,402 A | 7/1994 | Teitelbaum | |
| 5,411,552 A | 5/1995 | Andersen et al. | |
| 5,554,185 A | 9/1996 | Block et al. | |
| 5,718,725 A | 2/1998 | Sterman et al. | |
| 5,769,812 A | 6/1998 | Stevens et al. | |
| 5,797,960 A | 8/1998 | Stevens et al. | |
| 5,823,956 A | 10/1998 | Roth et al. | |
| 5,829,447 A | 11/1998 | Stevens et al. | |
| 5,840,081 A | 11/1998 | Andersen et al. | |
| 5,855,614 A | 1/1999 | Stevens et al. | |
| 6,174,322 B1 * | 1/2001 | Schneidt | A61B 17/0057 606/213 |
| 6,629,534 B1 * | 10/2003 | St. Goar | A61B 17/0469 128/898 |
| 7,033,390 B2 * | 4/2006 | Johnson | A61F 2/2412 623/2.11 |
| 7,291,168 B2 * | 11/2007 | Macoviak | A61F 2/2412 623/2.36 |
| 2002/0013571 A1 * | 1/2002 | Goldfarb | A61B 17/12 606/1 |
| 2002/0173841 A1 | 11/2002 | Ortiz et al. | |
| 2004/0049207 A1 * | 3/2004 | Goldfarb | A61B 50/30 606/139 |
| 2004/0087975 A1 * | 5/2004 | Lucatero | A61B 50/30 606/139 |
| 2004/0092858 A1 * | 5/2004 | Wilson | A61F 2/2418 604/9 |
| 2004/0092962 A1 * | 5/2004 | Thornton | A61B 50/30 606/139 |
| 2006/0015179 A1 * | 1/2006 | Bulman-Fleming | A61F 2/2442 623/2.36 |
| 2006/0089671 A1 * | 4/2006 | Goldfarb | A61B 17/122 606/215 |
| 2007/0197858 A1 * | 8/2007 | Goldfarb | A61B 17/0401 600/37 |
| 2008/0195126 A1 * | 8/2008 | Solem | A61F 2/24 606/155 |
| 2009/0163934 A1 * | 6/2009 | Raschdorf, Jr. | A61B 17/00234 606/139 |
| 2010/0121437 A1 * | 5/2010 | Subramanian | A61F 2/2445 623/2.36 |
| 2010/0262231 A1 * | 10/2010 | Tuval | A61F 2/2412 623/2.4 |
| 2010/0298929 A1 * | 11/2010 | Thornton | A61B 17/00234 623/2.1 |
| 2012/0179184 A1 * | 7/2012 | Orlov | A61B 90/02 606/170 |
| 2013/0066341 A1 * | 3/2013 | Ketai | A61B 17/08 606/151 |
| 2013/0066342 A1 * | 3/2013 | Dell | A61B 17/08 606/151 |
| 2014/0039511 A1 * | 2/2014 | Morris | A61B 17/083 606/110 |
| 2014/0350662 A1 * | 11/2014 | Vaturi | A61F 2/2412 623/2.1 |
| 2014/0358224 A1 * | 12/2014 | Tegels | A61L 27/14 623/2.14 |
| 2015/0051698 A1 * | 2/2015 | Ruyra Baliarda | A61F 2/2448 623/2.36 |
| 2015/0094800 A1 * | 4/2015 | Chawla | A61F 2/2457 623/2.1 |
| 2015/0230947 A1 * | 8/2015 | Krieger | A61F 2/2475 623/1.24 |
| 2015/0257877 A1 * | 9/2015 | Hernandez | A61F 2/2409 623/2.11 |

FOREIGN PATENT DOCUMENTS

| | | |
|---|---|---|
| WO | WO 98/35638 | 8/1998 |
| WO | WO 99/00059 | 1/1999 |
| WO | WO 99/01377 | 1/1999 |
| WO | WO 00/03759 | 1/2000 |
| WO | WO 00/60995 | 10/2000 |
| WO | WO 2004/006810 | 1/2004 |
| WO | WO 2004/103162 | 12/2004 |
| WO | WO 2006/113906 | 10/2006 |

OTHER PUBLICATIONS

Abe et al, De Vega's Annuloplasty for Acquired Tricuspid Disease: Early and Late Results in 110 Patients, Ann. Thorac. Surg., Jan. 1989, pp. 670-676, vol. 48.

Ali Khan et al, Blade Atrial Septostomy: Experience with the First 50 Procedures, Cathet. Cardiovasc. Diagn., Aug. 1991, pp. 257-262, vol. 23.

Alvarez et al, Repairing the Degenerative Mitral Valve: Ten to Fifteen-year Follow-up, J. Thorac. Cardiovasc. Surg., Aug. 1996, pp. 238-247, vol. 112.

Bach et al, Early Improvement in Congestive Heart Failure After Correction of Secondary Mitral Regurgitation in End-stage Cardiomyopathy, Am. Heart J., Jun. 1995, pp. 1165-1170, vol. 129.

Bach et al, Improvement Following Correction of Secondary Mitral Regurgitation in End-stage Cardiomyopathy With Mitral Annuloplasty, Am. J. Cardiol., Oct. 15, 1996, pp. 966-969, vol. 78.

Bolling et al, Surgery for Acquired Heart Disease: Early Outcome of Mitral Valve Reconstruction in Patients with End-stage Cardiomyopathy, J. Thor. and Cariovasc. Surg., Apr. 1995, pp. 676-683, vol. 109.

Dec et al, Idiopathic Dilated Cardiomyopathy, N. Engl. J. Med., Dec. 8, 1994, pp. 1564-1575, vol. 331.

Fucci et al, Improved Results with Mitral Valve Repair Using New Surgical Techniques, Eur. J. Cardiothorac. Surg., Nov. 1995, pp. 621-627, vol. 9.

Kameda et al, Annuloplasty for Severe Mitral Regurgitation Due to Dilated Cardiomyopathy, Ann. Thorac. Surg., 1996, pp. 1829-1832, vol. 61.

Maisano et al, The Edge-to-edge Technique: A Simplified Method to Correct Mitral Insufficiency, Eur. J. Cardiothorac. Surg., Jan. 14, 1998, pp. 240-246, vol. 13.

McCarthy et al, Tricuspid Valve Repair with the Cosgrove-Edwards Annuloplasty System, Ann. Thorac. Surg., Jan. 16, 1997, pp. 267-268, vol. 64.

Park et al, Clinical Use of Blade Atrial Septostomy, Circulation, 1978, pp. 600-608, vol. 58.

Ricchi et al, Linear Segmental Annuloplasty for Mitral Valve Repair, Ann. Thorac. Surg., Jan. 7, 1997, pp. 1805-1806, vol. 63.

Tager et al, Long-Term Follow-Up of Rheumatic Patients Undergoing Left-Sided Valve Replacement With Tricuspid Annuloplasty—Validity of Preoperative Echocardiographic Criteria in the Decision to Perform Tricuspid Annuloplasty, Am. J. Cardiol., Apr. 15, 1998, pp. 1013-1016, vol. 81.

Uchida et al, Percutaneous Cardiomyotomy and Valvulotomy with Angioscopic Guidance, Am. Heart J., Apr. 1991, pp. 1221-1224, vol. 121.

Umana et al, 'Bow-Tie' Mitral Valve Repair: An Adjuvant Technique for Ischemic Mitral Regurgitation, Ann. Thorac. Surg., May 12, 1998, pp. 1640-1646, vol. 66.

* cited by examiner

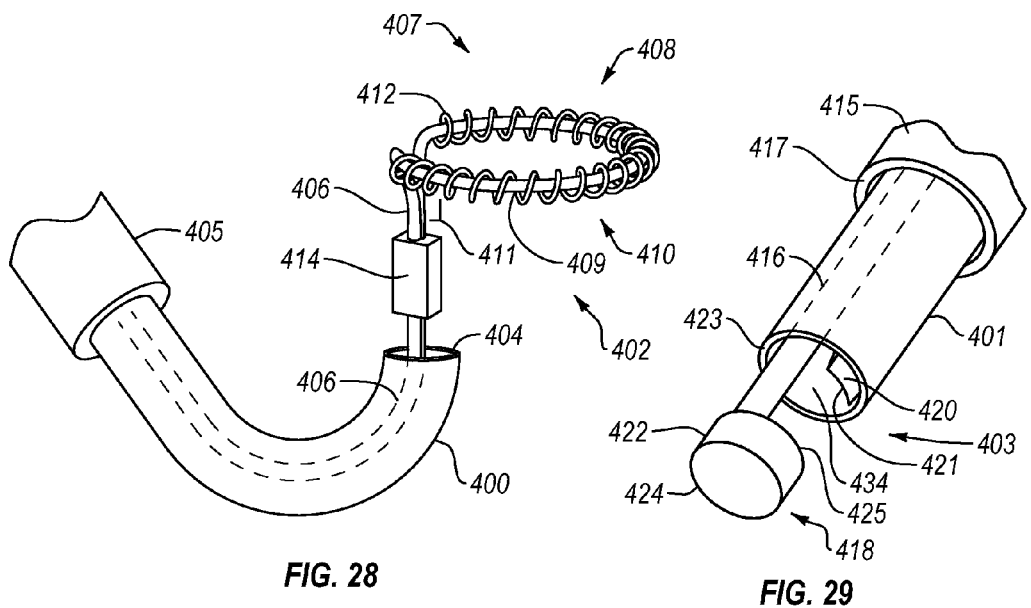
FIG. 28
FIG. 29
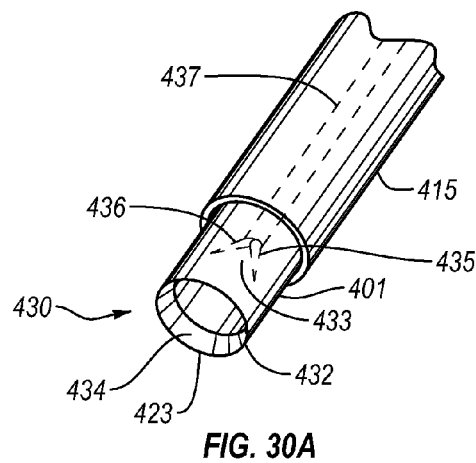
FIG. 30A

MITRAL VALVE FIXATION DEVICE REMOVAL DEVICES AND METHODS

CROSS-REFERENCE TO RELATED APPLICATIONS

NA

BACKGROUND

The present invention relates generally to medical methods, devices, and systems. In particular, the present invention relates to methods, devices, and systems for the endovascular, percutaneous or minimally invasive surgical treatment of bodily tissues, such as tissue approximation or valve repair. More particularly, the present invention relates to repair of valves of the heart and venous valves, and devices and methods for removing or disabling mitral valve repair components through minimally invasive procedures.

Surgical repair of bodily tissues often involves tissue approximation and fastening of such tissues in the approximated arrangement. When repairing valves, tissue approximation includes coapting the leaflets of the valves in a therapeutic arrangement which may then be maintained by fastening or fixing the leaflets. Such coaptation can be used to treat regurgitation which most commonly occurs in the mitral valve.

Mitral valve regurgitation is characterized by retrograde flow from the left ventricle of a heart through an incompetent mitral valve into the left atrium. During a normal cycle of heart contraction (systole), the mitral valve acts as a check valve to prevent flow of oxygenated blood back into the left atrium. In this way, the oxygenated blood is pumped into the aorta through the aortic valve. Regurgitation of the valve can significantly decrease the pumping efficiency of the heart, placing the patient at risk of severe, progressive heart failure.

Mitral valve regurgitation can result from a number of different mechanical defects in the mitral valve or the left ventricular wall. The valve leaflets, the valve chordae which connect the leaflets to the papillary muscles, the papillary muscles themselves or the left ventricular wall may be damaged or otherwise dysfunctional. Commonly, the valve annulus may be damaged, dilated, or weakened, limiting the ability of the mitral valve to close adequately against the high pressures of the left ventricle.

The most common treatments for mitral valve regurgitation rely on valve replacement or repair including leaflet and annulus remodeling, the latter generally referred to as valve annuloplasty. One technique for mitral valve repair which relies on suturing adjacent segments of the opposed valve leaflets together is referred to as the "bow-tie" or "edge-to-edge" technique. While all these techniques can be effective, they usually rely on open heart surgery where the patient's chest is opened, typically via a sternotomy, and the patient placed on cardiopulmonary bypass. The need to both open the chest and place the patient on bypass is traumatic and has associated high mortality and morbidity.

In some patients, a fixation device can be installed into the heart using minimally invasive techniques. The fixation device can hold the adjacent segments of the opposed valve leaflets together and may reduce mitral valve regurgitation. One such device used to clip the anterior and posterior leaflets of the mitral valve together is the MitraClip® fixation device, sold by Abbott Vascular, Santa Clara, Calif., USA.

However, sometimes after a fixation device is installed, undesirable mitral valve regurgitation can still exist, or can arise again. Further, other problems with the heart may arise that can make it desirable for the fixation device to be disabled or removed, usually in order that other procedures may be performed on the heart.

Current techniques for removing or disabling mitral valve fixation devices usually rely on open heart surgery where the patient's chest is opened, typically via a sternotomy, and the patient placed on cardiopulmonary bypass.

For these reasons, it would be desirable to provide alternative and additional methods, devices, and systems for removing or disabling fixation devices that are already installed. Such methods, devices, and systems should preferably not require open chest access and be capable of being performed either endovascularly, i.e., using devices which are advanced to the heart from a point in the patient's vasculature remote from the heart or by another minimally invasive approach. The methods, devices, and systems may be useful for repair of tissues in the body other than heart valves. At least some of these objectives will be met by the inventions described hereinbelow.

DESCRIPTION OF THE BACKGROUND ART

Minimally invasive and percutaneous techniques for coapting and modifying mitral valve leaflets to treat mitral valve regurgitation are described in PCT Publication Nos. WO 98/35638; WO 99/00059; WO 99/01377; and WO 00/03759; WO 2000/060995; WO 2004/103162. Maisano et al. (1998) Eur. J. Cardiothorac. Surg. 13:240-246; Fucci et al. (1995) Eur. J. Cardiothorac. Surg. 9:621-627; and Umana et al. (1998) Ann. Thorac. Surg. 66:1640-1646, describe open surgical procedures for performing "edge-to-edge" or "bow-tie" mitral valve repair where edges of the opposed valve leaflets are sutured together to lessen regurgitation. Dec and Fuster (1994) N. Engl. J. Med. 331:1564-1575 and Alvarez et al. (1996) J. Thorac. Cardiovasc. Surg. 112:238-247 are review articles discussing the nature of and treatments for dilated cardiomyopathy.

Mitral valve annuloplasty is described in the following publications: Bach and Bolling (1996) Am. J. Cardiol. 78:966-969; Kameda et al. (1996) Ann. Thorac. Surg. 61:1829-1832; Bach and Bolling (1995) Am. Heart J. 129: 1165-1170; and Bolling et al. (1995) 109:676-683. Linear segmental annuloplasty for mitral valve repair is described in Ricchi et al. (1997) Ann. Thorac. Surg. 63:1805-1806. Tricuspid valve annuloplasty is described in McCarthy and Cosgrove (1997) Ann. Thorac. Surg. 64:267-268; Tager et al. (1998) Am. J. Cardiol. 81:1013-1016; and Abe et al. (1989) Ann. Thorac. Surg. 48:670-676.

Percutaneous transluminal cardiac repair procedures are described in Park et al. (1978) Circulation 58:600-608; Uchida et al. (1991) Am. Heart J. 121: 1221-1224; and Ali Khan et al. (1991) Cathet. Cardiovasc. Diagn. 23:257-262. Endovascular cardiac valve replacement is described in U.S. Pat. Nos. 5,840,081; 5,411,552; 5,554,185; 5,332,402; 4,994,077; and 4,056,854. U.S. Pat. No. 3,671,979 describes a catheter for temporary placement of an artificial heart valve.

Other percutaneous and endovascular cardiac repair procedures are described in U.S. Pat. Nos. 4,917,089; 4,484,579; and 3,874,338; and PCT Publication No. WO 91/01689.

Thoracoscopic and other minimally invasive heart valve repair and replacement procedures are described in U.S. Pat. Nos. 5,855,614; 5,829,447; 5,823,956; 5,797,960; 5,769,812; and 5,718,725.

BRIEF SUMMARY

The present disclosure describes methods and devices that may be employed after a device that clips the anterior and posterior leaflets of the mitral valve together has been installed.

Sometimes after such a device is installed in the heart, problems may still exist or could arise with the function of the mitral valve or with the heart generally. In order to resolve these problems, it may be desirable to remove or disable the previously implanted device. It may also be desirable to perform a procedure on the mitral valve, such as mitral valve annuloplasty, balloon valvuloplasty, mitral valve repair, or installation of a replacement valve. In order to be able to perform procedures on a heart that already has a mitral valve fixation device attached thereto, it may be desirable to first remove or disable the device.

Traditionally, mitral valve fixation devices have been removed through invasive surgeries, such as open heart surgery. However, less invasive methods would be preferable, because, for example, persons with a mitral valve fixation device may not be suitable candidates for an invasive surgery. Disclosed herein are minimally invasive methods and devices that may be used in disabling or removing such a device.

For example, according to an embodiment, a method of disabling a fixation device that holds anterior and posterior leaflets of the mitral valve together is disclosed. The method may include partitioning (e.g., cutting) the fixation device so that an anterior distal element and an anterior gripping element of the fixation device remain attached to the anterior leaflet, and a posterior distal element and a posterior gripping element of the fixation device remain attached to the posterior leaflet.

According to another embodiment, a method of disabling a fixation device may include cutting one leaflet along or near the edges of a distal element and a gripping element of the fixation device so that the fixation device separates from a main portion of that leaflet from which it is cut.

Another method for removing a fixation device may include accessing, through an endovascular procedure, the fixation device holding the anterior and posterior leaflets of the mitral valve together. The endovascular procedure may advance a removal tool through the vasculature of the patient, and into the heart. The fixation device may be separated (e.g., cut) from both leaflets with the removal tool. The fixation device may then be removed from the body of the patient.

Any of such described methods may advantageously be performed with minimal invasion, e.g., through an endovascular procedure that advances any devices employed in the procedure (e.g., tools for cutting or otherwise separating the fixation device and/or surrounding tissue) through the vasculature of the patient, into the heart, where the devices may access the mitral valve.

Another method according to the present disclosure is directed to performing balloon valvuloplasty in a mitral valve including a fixation device that holds the anterior and posterior leaflets of the mitral valve together. The method may include positioning balloons in both orifices of the mitral valve and performing valvuloplasty in both orifices substantially simultaneously.

Another embodiment of the present disclosure is directed to an improved mitral clip fixation device for holding together anterior and posterior leaflets of the mitral valve during use. Such a device may include a pair of distal elements and a pair of gripping elements, each distal element and each gripping element having a respective first end and a respective free end opposite the first end. The first ends of each of the elements may be movably coupled together such that one distal element and one gripping element of the fixation device may be attached to the anterior leaflet during use. The other distal element and other gripping element of the fixation device may be attached to the posterior leaflet during use. The fixation device may further comprise a locking mechanism which locks at least the distal elements in place, wherein the locking mechanism includes a release harness. Application of tension to the release harness may unlock the locking mechanism. The release harness advantageously may extend from at or near the first ends of the distal elements and gripping elements, past the free ends of the distal elements, the free ends of the gripping elements, or both. Such a release harness is advantageously more easily accessible to the practitioner.

Another embodiment according to the present disclosure is directed to a system for disabling or removing a mitral valve fixation device. The system may include a catheter with cutting means disposed at the distal end of the catheter, the cutting means being configured to cut the fixation device and/or tissue surrounding the installed fixation device. The system may further include a catheter with retaining means disposed at the distal end of the catheter. The retaining means may be configured to retain the fixation device and/or cut portions thereof, so as to allow its removal through the catheter.

These and other objects and features of the present disclosure will become more fully apparent from the following description and appended claims, or may be learned by the practice of the embodiments of the invention as set forth hereinafter.

BRIEF DESCRIPTION OF THE DRAWINGS

To further clarify the above and other advantages and features of the present disclosure, a more particular description of the invention will be rendered by reference to specific embodiments thereof which are illustrated in the appended drawings. It is appreciated that these drawings depict only illustrated embodiments of the invention and are therefore not to be considered limiting of its scope. Embodiments of the invention will be described and explained with additional specificity and detail through the use of the accompanying drawings in which:

FIG. 28 illustrates an embodiment of a capture assembly for retaining at least a portion of a fixation device.

FIG. 29 illustrates an embodiment of a cutting assembly for cutting a fixation device and/or tissue surrounding the fixation device.

FIGS. 30A-30C illustrate another embodiment of a cutting assembly, another embodiment of a capturing device, an exemplary method of removing a fixing device.

DETAILED DESCRIPTION

I. Introduction

A. Cardiac Physiology

Figure 1:
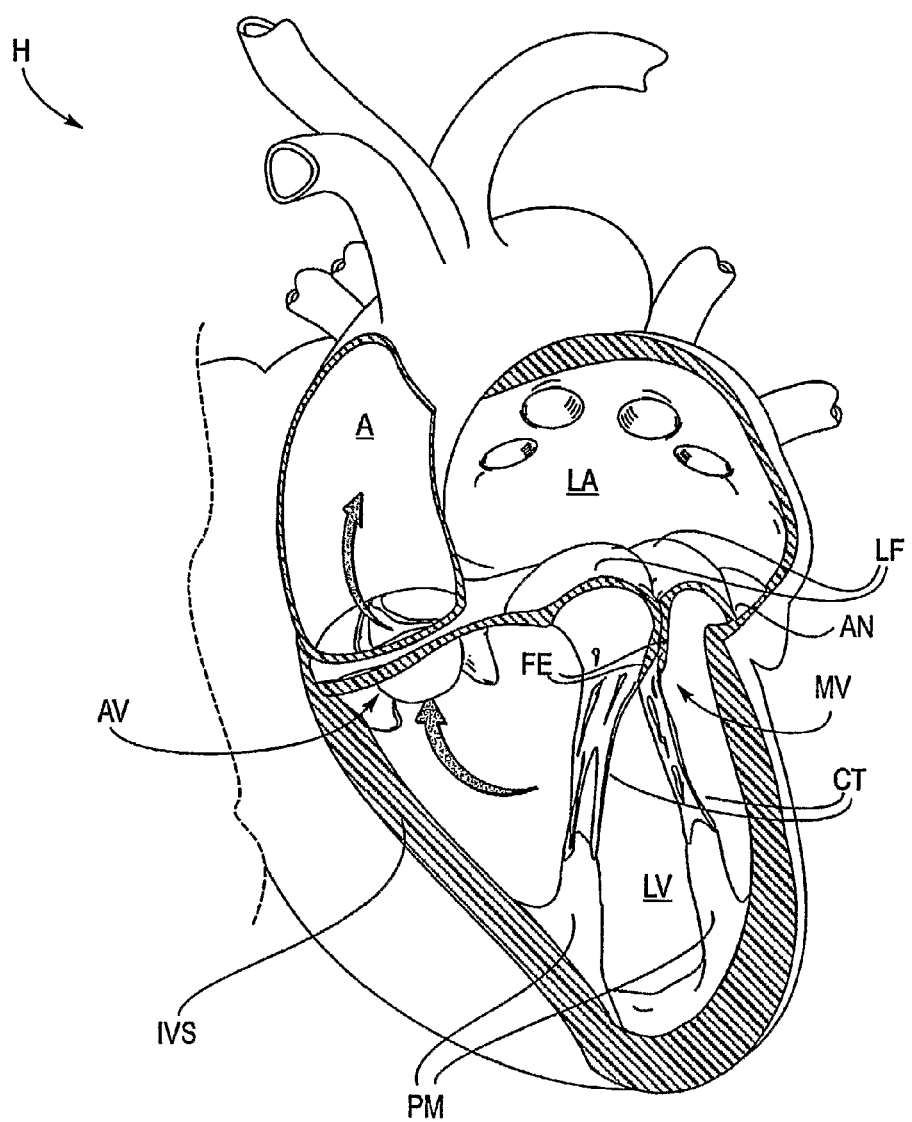
FIG. 1 illustrates the left ventricle and left atrium of the heart during systole.

The left ventricle (LV) of a normal heart H in systole is illustrated in FIG. 1. The left ventricle (LV) is contracting and blood flows outwardly through the tricuspid (aortic) valve (AV) in the direction of the arrows. Back flow of blood or "regurgitation" through the mitral valve (MV) is prevented since the mitral valve is configured as a "check valve" which prevents back flow when pressure in the left ventricle is higher than that in the left atrium (LA). The mitral valve (MV) comprises a pair of leaflets having free edges (FE) which meet evenly to close, as illustrated in FIG. 1. The opposite ends of the leaflets (LF) are attached to the surrounding heart structure along an annular region referred to as the annulus (AN). The free edges (FE) of the leaflets (LF) are secured to the lower portions of the left ventricle LV through chordae tendinae (CT) (referred to hereinafter as the chordae) which include a plurality of branching tendons secured over the lower surfaces of each of the valve leaflets (LF). The chordae (CT) in turn, are attached to the papillary muscles (PM) which extend upwardly from the lower portions of the left ventricle and intraventricular septum IVS.

Figure 2A:
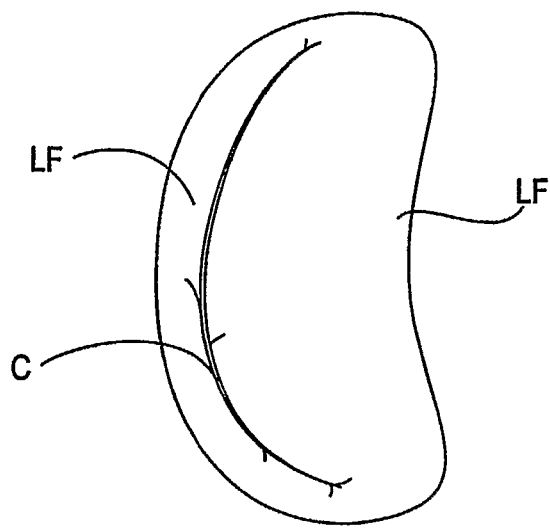
FIG. 2A illustrates free edges of leaflets of the mitral valve in normal coaptation.
Figure 2B:
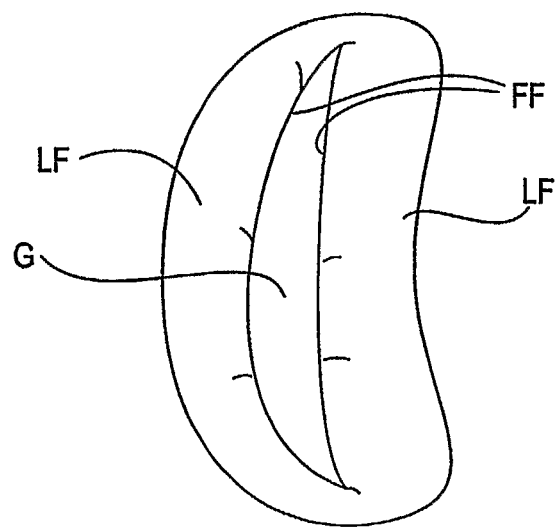
FIG. 2B illustrates the free edges in regurgitative coaptation.

A number of structural defects in the heart can cause mitral valve regurgitation. Regurgitation occurs when the valve leaflets do not close properly allowing leakage from the ventricle into the atrium. As shown in FIG. 2A, the free edges of the anterior and posterior leaflets normally meet along a line of coaptation (C). An example of a defect causing regurgitation is shown in FIG. 2B. Here an enlargement of the heart causes the mitral annulus to become enlarged, making it impossible for the free edges (FE) to meet during systole. This results in a gap (G) which allows blood to leak through the valve during ventricular systole. Ruptured or elongated chordae can also cause a valve leaflet to prolapse since inadequate tension is transmitted to the leaflet via the chordae. While the other leaflet maintains a normal profile, the two valve leaflets do not properly meet and leakage from the left ventricle into the left atrium will occur. Such regurgitation can also occur in patients who have suffered ischemic heart disease where the left ventricle does not contract sufficiently to effect proper closure.

II. General Overview of Mitral Valve Fixation Technology

Fixation devices are used for grasping, approximating and fixating tissues such as valve leaflets to treat cardiac valve regurgitation, particularly mitral valve regurgitation. The fixation devices may also provide features that allow repositioning and removal of the device if so desired, particularly in areas where removal may be hindered by anatomical features such as chordae CT. Such removal would allow the surgeon to reapproach the valve in a new manner if so desired.

Grasping will preferably be atraumatic providing a number of benefits. By atraumatic, it is meant that the devices and methods may be applied to the valve leaflets and then removed without causing any significant clinical impairment of leaflet structure or function. The leaflets and valve continue to function substantially the same as before the fixation devices are applied. Thus, some minor penetration or denting of the leaflets may occur using the devices while still meeting the definition of "atraumatic." Similarly, during disabling or removal of the fixation device, a small portion of the leaflet(s) may be cut around the edges of the fixation device. Such atraumatic installation, disabling, or removal enables the devices to be applied to a diseased valve and, if desired, removed or repositioned without having negatively affected valve function. In addition, it will be understood that in some cases it may be necessary or desirable to pierce or otherwise permanently affect the leaflets during either grasping, fixing and/or removal. In some cases, grasping and fixation may be accomplished by a single device.

The fixation devices may rely upon the use of an interventional tool that is positioned near a desired treatment site and used to grasp the target tissue. In endovascular applications, the interventional tool is typically an interventional catheter. In surgical applications, the interventional tool is typically an interventional instrument. Fixation of the grasped tissue is accomplished by maintaining grasping with a portion of the interventional tool which is left behind as an implant. The fixation devices are well adapted for the repair of valves, especially cardiac valves such as the mitral valve.

Figure 3A:
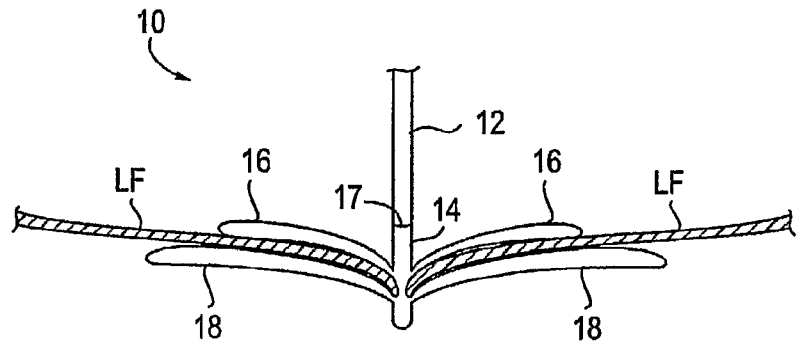
FIGS. 3A-3C illustrate grasping of the leaflets with a fixation device, inversion of the distal elements of the fixation device and removal of the fixation device, respectively.

Referring to FIG. 3A, an interventional tool 10, having a delivery device, such as a shaft 12, and a fixation device 14, is illustrated having approached the mitral valve MV from the atrial side and grasped the leaflets LF. The mitral valve may be accessed either surgically or by using endovascular techniques, and either by a retrograde approach through the ventricle or by an antegrade approach through the atrium, as described above. For illustration purposes, an antegrade approach is described.

The fixation device 14 is releasably attached to the shaft 12 of the interventional tool 10 at its distal end. When describing the devices of the invention herein, "proximal" shall mean the direction toward the end of the device to be manipulated by the user outside the patient's body, and "distal" shall mean the direction toward the working end of the device that is positioned at the treatment site and away from the user. With respect to the mitral valve, proximal shall refer to the atrial or upstream side of the valve leaflets and distal shall refer to the ventricular or downstream side of the valve leaflets.

The fixation device 14 typically comprises proximal elements 16 (or gripping elements) and distal elements 18 (or fixation elements) which protrude radially outward and are positionable on opposite sides of the leaflets LF as shown so as to capture or retain the leaflets therebetween. The proximal elements 16 are preferably comprised of cobalt chromium, nitinol or stainless steel, and the distal elements 18 are preferably comprised of cobalt chromium or stainless steel, however any suitable materials may be used. The fixation device 14 is coupleable to the shaft 12 by a coupling mechanism 17. The coupling mechanism 17 allows the fixation device 14 to detach and be left behind as an implant to hold the leaflets together in the coapted position.

In some situations, it may be desired to reposition or remove the fixation device 14 after the proximal elements 16, distal elements 18, or both have been deployed to capture the leaflets LF. Such repositioning or removal may be desired for a variety of reasons, such as to reapproach the valve in an attempt to achieve better valve function, more optimal positioning of the device 14 on the leaflets, better purchase on the leaflets, to detangle the device 14 from surrounding tissue such as chordae, to exchange the device 14 with one having a different design, or to abort the fixation procedure, to name a few. To facilitate repositioning or removal of the fixation device 14 the distal elements 18 may be released and optionally inverted to a configuration suitable for withdrawal of the device 14 from the valve without tangling or interfering with or damaging the chordae, leaflets or other tissue. According to another embodiment, any of the endovascular methods described herein for disabling or removal of the fixation device may also be used.

Figure 3B:
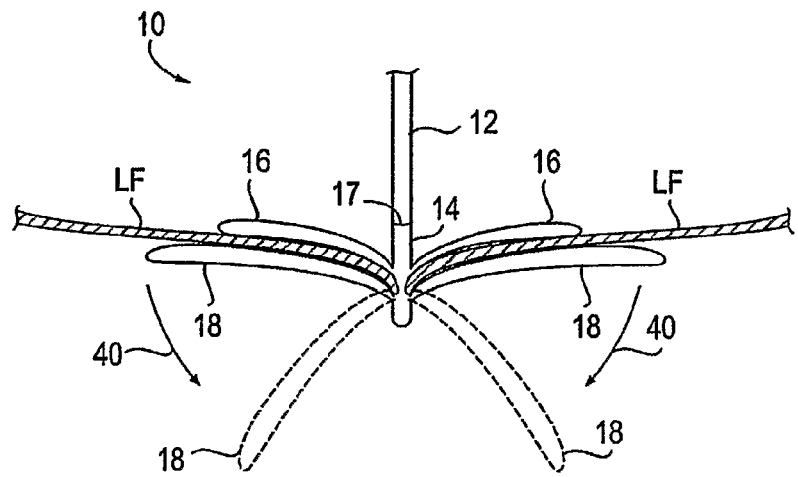
Figure 3C:
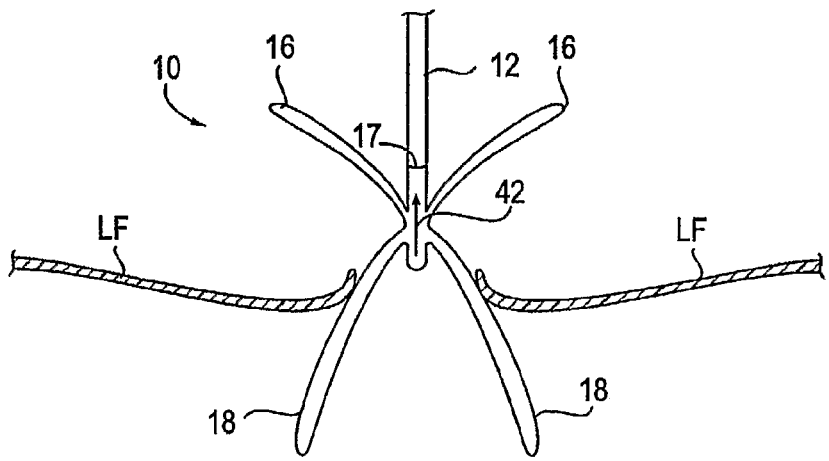

FIG. 3B illustrates inversion wherein the distal elements 18 are moveable in the direction of arrows 40 to an inverted position. Likewise, the proximal elements 16 may be raised, if desired. In the inverted position, the device 14 may be repositioned to a desired orientation wherein the distal elements may then be reverted to a grasping position against the leaflets as in FIG. 3A. Alternatively, the fixation device 14 may be withdrawn (indicated by arrow 42) from the leaflets as shown in FIG. 3C. Such inversion reduces trauma to the leaflets and minimizes any entanglement of the device with surrounding tissues. Once the device 14 has been withdrawn through the valve leaflets, the proximal and distal elements may be moved to a closed position or configuration suitable for removal from the body or for reinsertion through the mitral valve.

Figure 4:
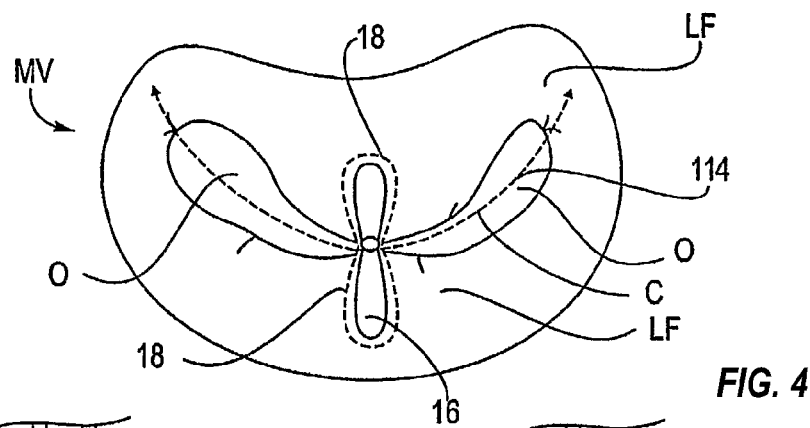
FIG. 4 illustrates the position of the fixation device in a desired orientation relative to the leaflets.

FIG. 4 illustrates the position of the fixation device 14 in a desired orientation in relation to the leaflets LF. This is a short-axis view of the mitral valve MV from the atrial side, therefore, the proximal elements 16 are shown in solid line and the distal elements 18 are shown in dashed line. The proximal and distal elements 16, 18 are positioned to be substantially perpendicular to the line of coaptation C. The device 14 may be moved roughly along the line of coaptation to the location of regurgitation. The leaflets LF are held in place so that during diastole, as shown in FIG. 4, the leaflets LF remain in position between the elements 16, 18 surrounded by openings or orifices O which result from the diastolic pressure gradient. Advantageously, leaflets LF are coapted such that their proximal or upstream surfaces are facing each other in a vertical orientation, parallel to the direction of blood flow through mitral valve MV. The upstream surfaces may be brought together so as to be in contact with one another or may be held slightly apart, but will preferably be maintained in the vertical orientation in which the upstream surfaces face each other at the point of coaptation. This simulates the double orifice geometry of a standard surgical bow-tie repair. Color Doppler echo will show if the regurgitation of the valve has been reduced. If the resulting mitral flow pattern is satisfactory, the leaflets may be fixed together in this orientation. If the resulting color Doppler image shows insufficient improvement in mitral regurgitation, the interventional tool 10 may be repositioned. This may be repeated until an optimal result is produced wherein the leaflets LF are held in place.

Figure 5A:
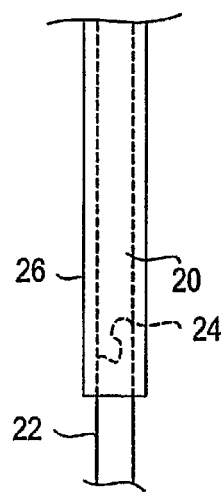
FIGS. 5A-5B, 6A-6B illustrate exemplary coupling mechanisms for coupling the fixation device to a shaft of a delivery catheter.
Figure 5B:
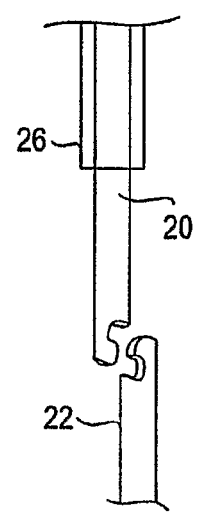

Once the leaflets are coapted in the desired arrangement, the fixation device 14 is then detached from the shaft 12 and left behind as an implant to hold the leaflets together in the coapted position. As mentioned previously, the fixation device 14 is coupled to the shaft 12 by a coupling mechanism 17. FIGS. 5A-5B, 6A-6B illustrate examples of such coupling mechanisms. FIG. 5A shows an upper shaft 20 and a detachable lower shaft 22 which are interlocked at a joining line or mating surface 24. The mating surface 24 may have any shape or curvature which will allow or facilitate interlocking and later detachment. A snuggly fitting outer sheath 26 is positioned over the shafts 20, 22 to cover the mating surface 24 as shown. FIG. 5B illustrates detachment of the lower shaft 22 from the upper shaft 20. This is achieved by retracting the outer sheath 26, so that the mating surface 24 is exposed, which allows the shafts 20, 22 to separate.

Figure 6A:
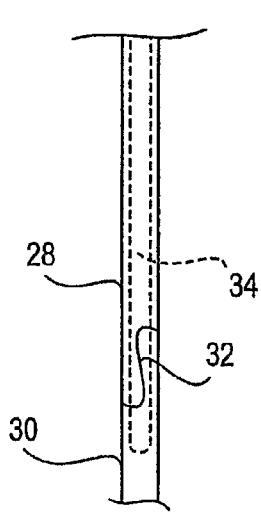
Figure 6B:
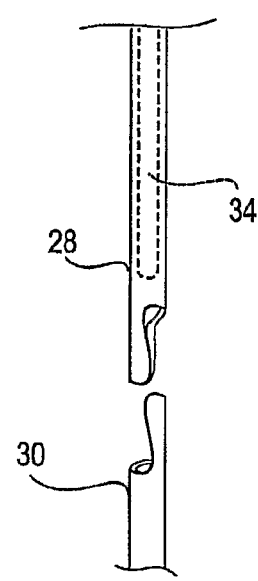

Similarly, FIG. 6A illustrates a tubular upper shaft 28 and a detachable tubular lower shaft 30 which are interlocked at a mating surface 32. Again, the mating surface 32 may have any shape or curvature which will allow or facilitate interlocking and later detachment. The tubular upper shaft 28 and tubular lower shaft 30 form an outer member having an axial channel. A snuggly fitting rod 34 or inner member is inserted through the tubular shafts 28, 30 to bridge the mating surface 32 as shown. FIG. 6B illustrates detachment of the lower shaft 30 from the upper shaft 28. This is achieved by retracting the rod 34 to a position above the mating surface 32 which in turn allows the shafts 28, 30 to separate.

The mating surface 24 (or mating surface 32) is a sigmoid curve defining a male element and female element on upper shaft 20 (or upper shaft 28) which interlock respectively with corresponding female and male elements on lower shaft 22 (or lower shaft 30). Typically, the lower shaft is the coupling mechanism 17 of the fixation device 14. Therefore, the shape of the mating surface selected will preferably provide at least some mating surfaces transverse to the axial axis of the mechanism 19 to facilitate application of compressive and tensile forces through the coupling mechanism 17 to the fixation device 14, yet causing minimal interference when the fixation device 14 is to be released from the upper shaft. It will be appreciated that these coupling mechanisms are exemplary, and other coupling mechanisms could also be used.

A. Exemplary Fixation Device

Figure 7:
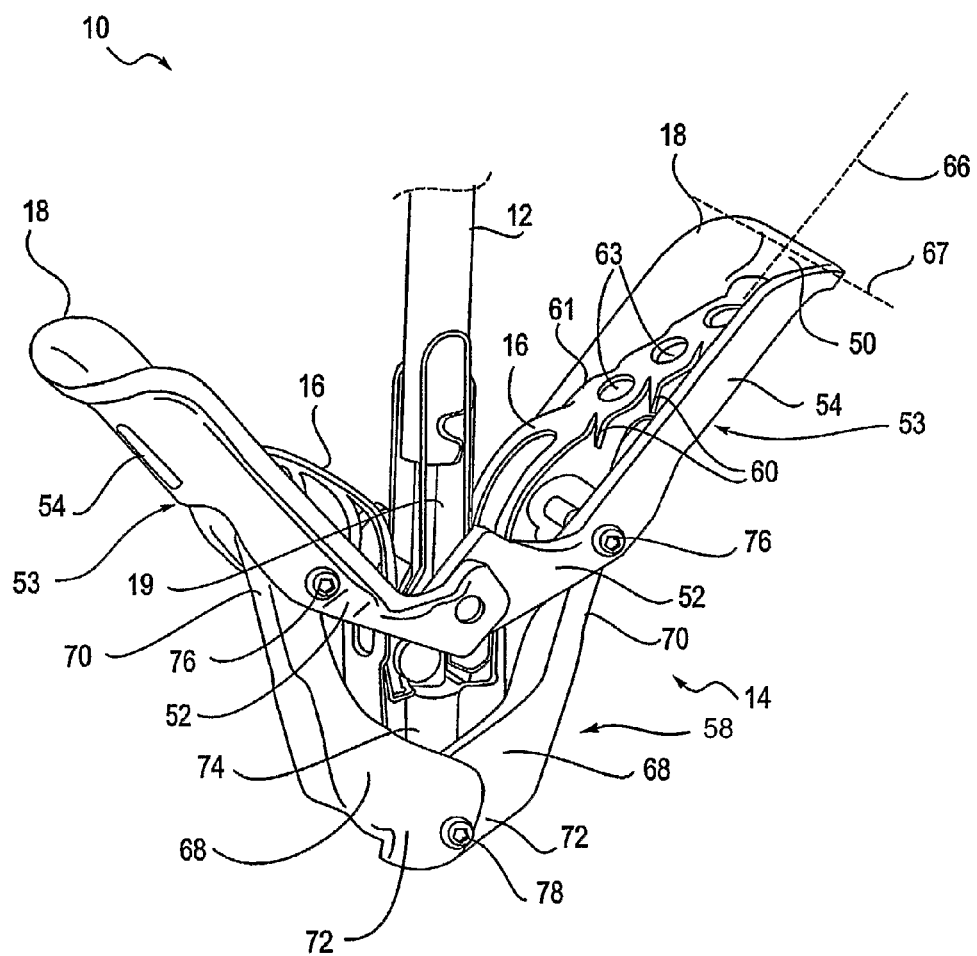
FIG. 7 illustrates an exemplary fixation device coupled to a shaft.

FIG. 7 illustrates an exemplary fixation device 14. Here, the fixation device 14 is shown coupled to a shaft 12 to form an interventional tool 10. The fixation device 14 includes a coupling member 19 and a pair of opposed distal elements 18. The distal elements 18 comprise elongate arms 53, each arm having a proximal end 52 rotatably connected to the coupling member 19 and a free end 54. The free ends 54 have a rounded shape to minimize interference with and trauma to surrounding tissue structures. Preferably, each free end 54 defines a curvature about two axes, one being an axis 66 perpendicular to longitudinal axis of arms 53. Thus, the engagement surfaces 50 have a cupped or concave shape to the surface area in contact with tissue and to assist in grasping and holding the valve leaflets. This further allows arms 53 to nest around the shaft 12 in the closed position to minimize the profile of the device. Preferably, arms 53 are at least partially cupped or curved inwardly about their longitudinal axes 66. Also, preferably, each free end 54 defines a curvature about an axis 67 perpendicular to axis 66 or the longitudinal axis of arms 53. This curvature is a reverse curvature along the most distal portion of the free end 54. Likewise, the longitudinal edges of the free ends 54 may flare outwardly. Both the reverse curvature and flaring minimize trauma to the tissue engaged therewith.

To be suitable for mitral valve repair, the transverse width across engagement surfaces 50 (which determines the width of tissue engaged) may be at least about 2 mm, usually 3-10 mm, and preferably about 4-6 mm. In some situations, a wider engagement is desired wherein the engagement surfaces 50 are larger, for example about 2 cm, or multiple fixation devices are used adjacent to each other. Arms 53 and engagement surfaces 50 are configured to engage a length of tissue of about 4-10 mm, and preferably about 6-8 mm along the longitudinal axis of arms 53. Arms 53 further include a plurality of openings to enhance grip and to promote tissue ingrowth following implantation.

The valve leaflets are grasped between the distal elements 18 and proximal elements 16. The proximal elements 16 may be flexible, resilient, and cantilevered from coupling member 19. The proximal elements are preferably resiliently biased toward the distal elements. Each proximal element 16 is shaped and positioned to be at least partially recessed within the concavity of the distal element 18 when no tissue is present. When the fixation device 14 is in the open position, the proximal elements 16 are shaped such that each proximal element 16 is separated from the engagement surface 50 near the proximal end 52 of arm 53 and slopes toward the engagement surface 50 near the free end 54 with the free end of the proximal element contacting engagement surface 50, as illustrated in FIG. 7. This shape of the proximal elements 16 accommodates valve leaflets or other tissues of varying thicknesses.

Proximal elements 16 include a plurality of openings 63 and scalloped side edges 61 to increase grip on tissue. The proximal elements 16 optionally include frictional accessories, frictional features or grip-enhancing elements to assist in grasping and/or holding the leaflets. The frictional accessories may comprise barbs 60 having tapering pointed tips extending toward engagement surfaces 50. Any suitable frictional accessories may be used, such as prongs, windings, bands, barbs, grooves, channels, bumps, surface roughening, sintering, high-friction pads, coverings, coatings or a combination of these. Optionally, magnets may be present in the proximal and/or distal elements. It may be appreciated that the mating surfaces will be made from or will include material of opposite magnetic charge to cause attraction by magnetic force. For example, the proximal elements and distal elements may each include magnetic material of opposite charge so that tissue is held under constant compression between the proximal and distal elements to facilitate faster healing and ingrowth of tissue. Also, the magnetic force may be used to draw the proximal elements 16 toward the distal elements 18, in addition to or alternatively to biasing of the proximal elements toward the distal elements. This may assist in deployment of the proximal elements 16. In another example, the distal elements 18 each include magnetic material of opposite charge so that tissue positioned between the distal elements 18 is held therebetween by magnetic force.

The proximal elements 16 may be covered with a fabric or other flexible material as described below to enhance grip and tissue ingrowth following implantation. Preferably, when fabrics or coverings are used in combination with barbs or other frictional features, such features will protrude through such fabric or other covering so as to contact any tissue engaged by proximal elements 16.

Proximal elements 16 may be formed from metallic sheet of a spring-like material using a stamping operation which creates openings 63, scalloped edges 61 and barbs 60. Alternatively, proximal elements 16 could be comprised of a spring-like material or molded from a biocompatible polymer. Some types of frictional accessories may permanently alter or cause some trauma to the tissue engaged thereby, whereas other frictional accessories will be atraumatic and will not injure or otherwise affect the tissue in a clinically significant way. For example, in the case of barbs 60, it has been demonstrated that following engagement of mitral valve leaflets by fixation device 14, should the device later be removed during the procedure barbs 60 leave no significant permanent scarring or other impairment of the leaflet tissue and are thus considered atraumatic.

The fixation device 14 also includes an actuation mechanism 58. The actuation mechanism 58 comprises two link members or legs 68, each leg 68 having a first end 70 which is rotatably joined with one of the distal elements 18 at a riveted joint 76 and a second end 72 which is rotatably joined with a stud 74. The legs 68 are preferably comprised of a rigid or semi-rigid metal or polymer such as Elgiloy®, cobalt chromium or stainless steel, however any suitable material may be used. While in the device illustrated both legs 68 are pinned to stud 74 by a single rivet 78, it may be appreciated, however, that each leg 68 may be individually attached to the stud 74 by a separate rivet or pin. The stud 74 is joinable with an actuator rod 64 (not shown) which extends through the shaft 12 and is axially extendable and retractable to move the stud 74 and therefore the legs 68 which rotate the distal elements 18 between closed, open and inverted positions. Likewise, immobilization of the stud 74 holds the legs 68 in place and therefore holds the distal elements 18 in a desired position. The stud 74 may also be locked in place by a locking feature which will be further described in later sections.

There may be some mobility or flexibility in distal elements 18 and/or proximal elements 16 of the fixation device 14 in the closed position to enable these elements to move or flex with the opening or closing of the valve leaflets. This provides shock absorption and thereby reduces force on the leaflets and minimizes the possibility for tearing or other trauma to the leaflets. Such mobility or flexibility may be provided by using a flexible, resilient metal or polymer of appropriate thickness to construct the distal elements 18. Also, the locking mechanism of the fixation device (described below) may be constructed of flexible materials to allow some slight movement of the proximal and distal elements even when locked. Further, the distal elements 18 can be connected to the coupling mechanism 19 or to actuation mechanism 58 by a mechanism that biases the distal element into the closed position (inwardly) but permits the arms to open slightly in response to forces exerted by the leaflets. For example, rather than being pinned at a single point, these components may be pinned through a slot that allows a small amount of translation of the pin in response to forces against the arms. A spring may be used to bias the pinned component toward one end of the slot.

Figure 8A:
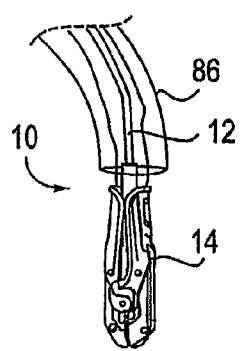
FIGS. 8A-8B, 9A-9B, 10A-10B, 11A-11B, and FIGS. 12-14 illustrate a fixation device in various possible positions during introduction and placement of the device within the body to perform a therapeutic procedure.
Figure 8B:
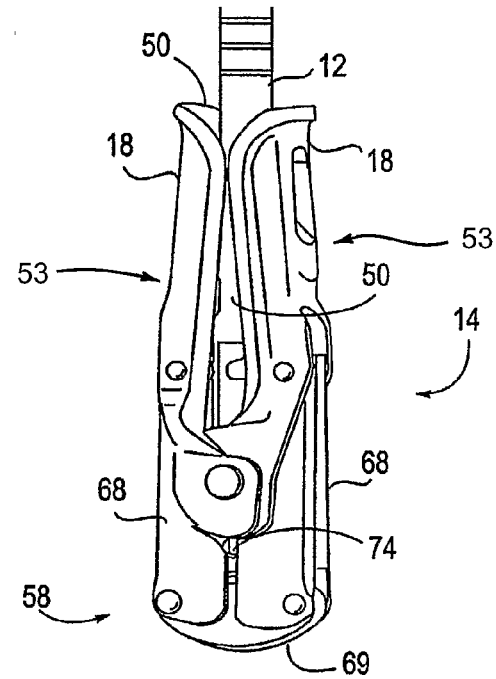

FIGS. 8A-8B, 9A-9B, 10A-10B, 11A-11B, and FIGS. 12-14 illustrate various possible positions of the fixation device 14 of FIG. 7 during introduction and placement of the device 14 within the body to perform a therapeutic procedure. FIG. 8A illustrates an interventional tool 10 delivered through a catheter 86. It may be appreciated that the interventional tool 10 may take the form of a catheter, and likewise, the catheter 86 may take the form of a guide catheter or sheath. However, in this example the terms interventional tool 10 and catheter 86 will be used. The interventional tool 10 comprises a fixation device 14 coupled to a shaft 12 and the fixation device 14 is shown in the closed position. FIG. 8B illustrates a device similar to the device of FIG. 8A in a larger view. In the closed position, the opposed pair of distal elements 18 are positioned so that the engagement surfaces 50 face each other. Each distal element 18 comprises an elongate arm 53 having a cupped or concave shape so that together the arms 53 surround the shaft 12 and optionally contact each other on opposite sides of the shaft. This provides a low profile for the fixation device 14 which is readily passable through the catheter 86 and through any anatomical structures, such as the mitral valve. In addition, FIG. 8B further includes an actuation mechanism 58. The actuation mechanism 58 comprises two legs 68 which are each movably coupled to a base 69. The base 69 is joined with an actuator rod 64 which extends through the shaft 12 and is used to manipulate the fixation device 14. The actuator rod 64 may attach directly to the actuation mechanism 58, particularly the base 69. However, the actuator rod 64 may alternatively attach to a stud 74 which in turn is attached to the base 69. The stud 74 may be threaded so that the actuator rod 64 attaches to the stud 74 by a screw-type action. However, the rod 64 and stud 74 may be joined by any mechanism which is releasable to allow the fixation device 14 to be detached from shaft 12.

Figure 9A:
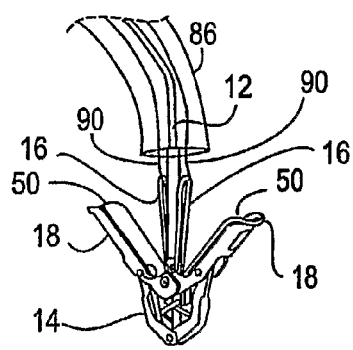
Figure 9B:
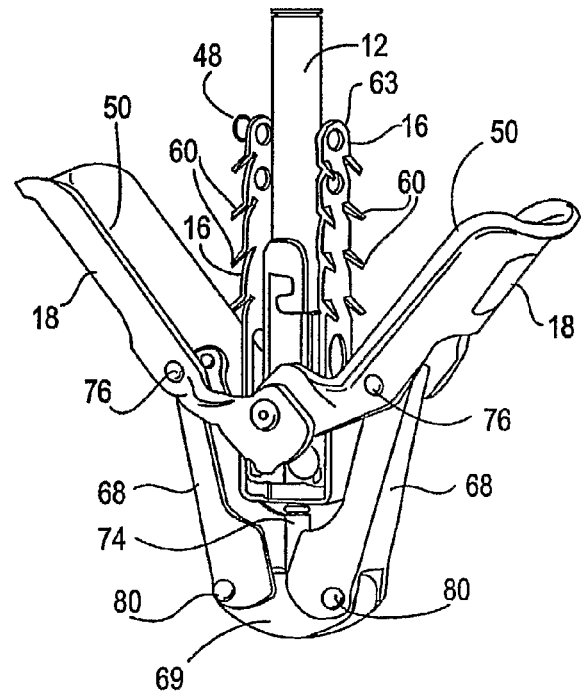

FIGS. 9A-9B illustrate the fixation device 14 in the open position. In the open position, the distal elements 18 are rotated so that the engagement surfaces 50 face a first direction. Distal advancement of the stud 74 relative to coupling member 19 by action of the actuator rod 64 applies force to the distal elements 18 which begin to rotate around joints 76 due to freedom of movement in this direction. Such rotation and movement of the distal elements 18 radially outward causes rotation of the legs 68 about joints 80 so that the legs 68 are directed slightly outwards. The stud 74 may be advanced to any desired distance correlating to a desired separation of the distal elements 18. In the open position, engagement surfaces 50 are disposed at an acute angle relative to shaft 12, and are preferably at an angle of between 90 and 180 degrees relative to each other. In the open position, the free ends 54 of arms 53 may have a span therebetween of about 10-20 mm, usually about 12-18 mm, and preferably about 14-16 mm.

Proximal elements 16 are typically biased outwardly toward arms 53. The proximal elements 16 may be moved inwardly toward the shaft 12 and held against the shaft 12 with the aid of proximal element lines 90 which can be in the form of sutures, wires, nitinol wire, rods, cables, polymeric lines, or other suitable structures. The proximal element lines 90 may be connected with the proximal elements 16 by threading the lines 90 in a variety of ways. When the proximal elements 16 have a loop shape, as shown in FIG. 9A, the line 90 may pass through the loop and double back. When the proximal elements 16 have an elongate solid shape, as shown in FIG. 9B, the line 90 may pass through one or more of the openings 63 in the element 16. Further, a line loop 48 may be present on a proximal element 16, also illustrated in FIG. 9B, through which a proximal element line 90 may pass and double back. Such a line loop 48 may be useful to reduce friction on proximal element line 90 or when the proximal elements 16 are solid or devoid of other loops or openings through which the proximal element lines 90 may attach. A proximal element line 90 may attach to the proximal elements 16 by detachable means which would allow a single line 90 to be attached to a proximal element 16 without doubling back and would allow the single line 90 to be detached directly from the proximal element 16 when desired. Examples of such detachable means include hooks, snares, clips or breakable couplings, to name a few.

By applying sufficient tension to the proximal element line 90, the detachable means may be detached from the proximal element 16 such as by breakage of the coupling. Other mechanisms for detachment may also be used. Similarly, a lock line 92 (FIG. 16) may be attached and detached from a locking mechanism by similar detachable means.

In the open position, the fixation device 14 can engage the tissue which is to be approximated or treated. The device illustrated in FIGS. 7-9B is adapted for repair of the mitral valve using an antegrade approach from the left atrium. The interventional tool 10 is advanced through the mitral valve from the left atrium to the left ventricle. The distal elements 18 are oriented to be perpendicular to the line of coaptation and then positioned so that the engagement surfaces 50 contact the ventricular surface of the valve leaflets, thereby grasping the leaflets. The proximal elements 16 remain on the atrial side of the valve leaflets so that the leaflets lie between the proximal and distal elements. The proximal elements 16 have frictional accessories, such as barbs 60 which are directed toward the distal elements 18. However, neither the proximal elements 16 nor the barbs 60 contact the leaflets at this time.

The interventional tool 10 may be repeatedly manipulated to reposition the fixation device 14 so that the leaflets are properly contacted or grasped at a desired location. Repositioning is achieved with the fixation device in the open position. In some instances, regurgitation may also be checked while the device 14 is in the open position. If regurgitation is not satisfactorily reduced, the device may be repositioned and regurgitation checked again until the desired results are achieved.

Figure 10A:
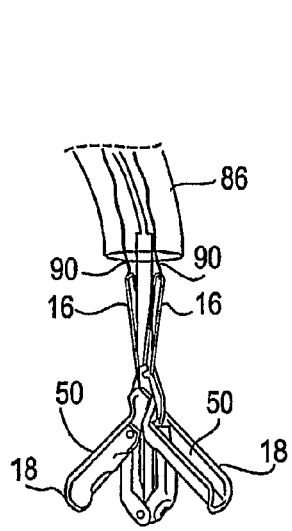
Figure 10B:
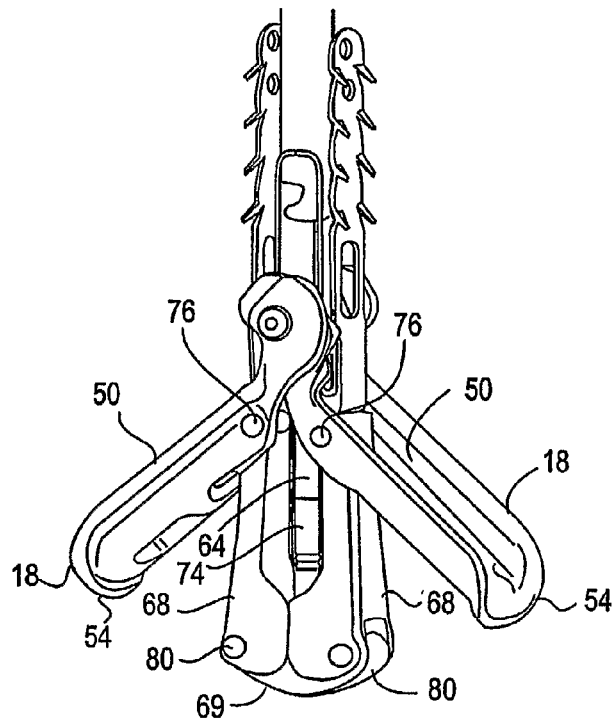

It may also be desired to invert the fixation device 14 to aid in repositioning or removal of the fixation device 14. FIGS. 10A-10B illustrate the fixation device 14 in the inverted position. By further advancement of stud 74 relative to coupling member 19, the distal elements 18 are further rotated so that the engagement surfaces 50 face outwardly and free ends 54 point distally, with each arm 53 forming an obtuse angle relative to shaft 12.

The angle between arms 53 is preferably in the range of about 270 to 360 degrees. Further advancement of the stud 74 further rotates the distal elements 18 around joints 76. This rotation and movement of the distal elements 18 radially outward causes rotation of the legs 68 about joints 80 so that the legs 68 are returned toward their initial position, generally parallel to each other. The stud 74 may be advanced to any desired distance correlating to a desired inversion of the distal elements 18. Preferably, in the fully inverted position, the span between free ends 54 is no more than about 20 mm, usually less than about 16 mm, and preferably about 12-14 mm. In this illustration, the proximal elements 16 remain positioned against the shaft 12 by exerting tension on the proximal element lines 90. Thus, a relatively large space may be created between the elements 16, 18 for repositioning. In addition, the inverted position allows withdrawal of the fixation device 14 through the valve while minimizing trauma to the leaflets. Engagement surfaces 50 provide an atraumatic surface for deflecting tissue as the fixation device is retracted proximally. Barbs 60 are angled slightly in the distal direction (away from the free ends of the proximal elements 16), reducing the risk that the barbs will catch on or lacerate tissue as the fixation device is withdrawn.

Figure 11A:
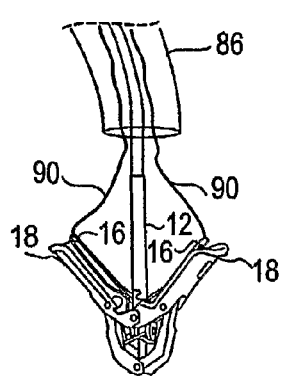
Figure 11B:
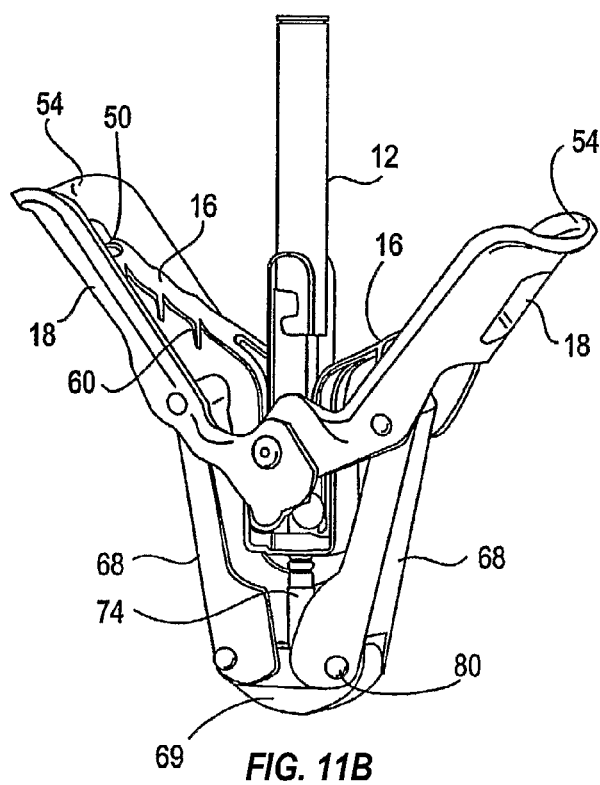

Once the fixation device 14 has been positioned in a desired location against the valve leaflets, the leaflets may then be captured between the proximal elements 16 and the distal elements 18. FIGS. 11A-11B illustrate the fixation device 14 in such a position. Here, the proximal elements 16 are lowered toward the engagement surfaces 50 so that the leaflets are held therebetween. In FIG. 11B, the proximal elements 16 are shown to include barbs 60 which may be used to provide atraumatic gripping of the leaflets. Alternatively, larger, more sharply pointed barbs or other penetration structures may be used to pierce the leaflets to more actively assist in holding them in place. This position is similar to the open position of FIGS. 9A-9B, however the proximal elements 16 are now lowered toward arms 53 by releasing tension on proximal element lines 90 to compress the leaflet tissue therebetween. At any time, the proximal elements 16 may be raised and the distal elements 18 adjusted or inverted to reposition the fixation device 14, if regurgitation is not sufficiently reduced.

Figure 12:
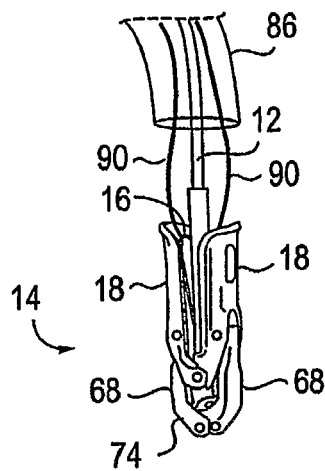

After the leaflets have been captured between the proximal and distal elements 16, 18 in a desired arrangement, the distal elements 18 may be locked to hold the leaflets in this position or the fixation device 14 may be returned to or toward a closed position. Such locking will be described in a later section. FIG. 12 illustrates the fixation device 14 in the closed position wherein the leaflets (not shown) are captured and coapted. This is achieved by retraction of the stud 74 proximally relative to coupling member 19 so that the legs 68 of the actuation mechanism 58 apply an upwards force to the distal elements 18 which in turn rotate the distal elements 18 so that the engagement surfaces 50 again face one another. The released proximal elements 16 which are biased outwardly toward distal elements 18 are concurrently urged inwardly by the distal elements 18. The fixation device 14 may then be locked to hold the leaflets in this closed position as described below.

Figure 13:
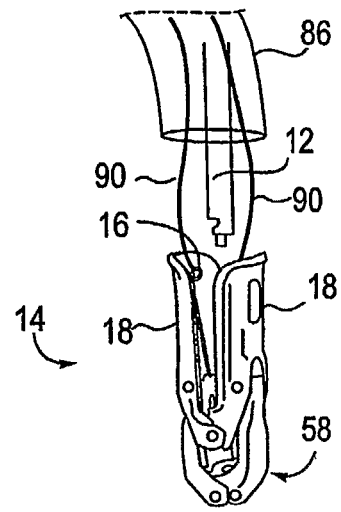

As shown in FIG. 13, the fixation device 14 may then be released from the shaft 12. As mentioned, the fixation device 14 is releasably coupleable to the shaft 12 by coupling member 19. FIG. 13 illustrates the coupling structure, a portion of the shaft 12 to which the coupling member 19 of the fixation device 14 attaches. As shown, the proximal element lines 90 may remain attached to the proximal elements 16 following detachment from shaft 12 to function as a tether to keep the fixation device 14 connected with the catheter 86. Optionally, a separate tether coupled between shaft 12 and fixation device 14 may be used expressly for this purpose while the proximal element lines 90 are removed. In any case, the repair of the leaflets or tissue may have been observed by non-invasive visualization techniques, such as echocardiography, to ensure the desired outcome. Then if the repair was not as desired, the fixation device 14 could be retrieved with the use of the tether or proximal element lines 90 so as to reconnect coupling member 19 with shaft 12.

The proximal element lines 90 may be elongated flexible threads, wire, cable, sutures or lines extending through shaft 12, looped through proximal elements 16, and extending back through shaft 12 to its proximal end. When detachment is desired, one end of each line may be released at the proximal end of the shaft 12 and the other end pulled to draw the free end of the line distally through shaft 12 and through proximal element 16 thereby releasing the fixation device.

Figure 14:
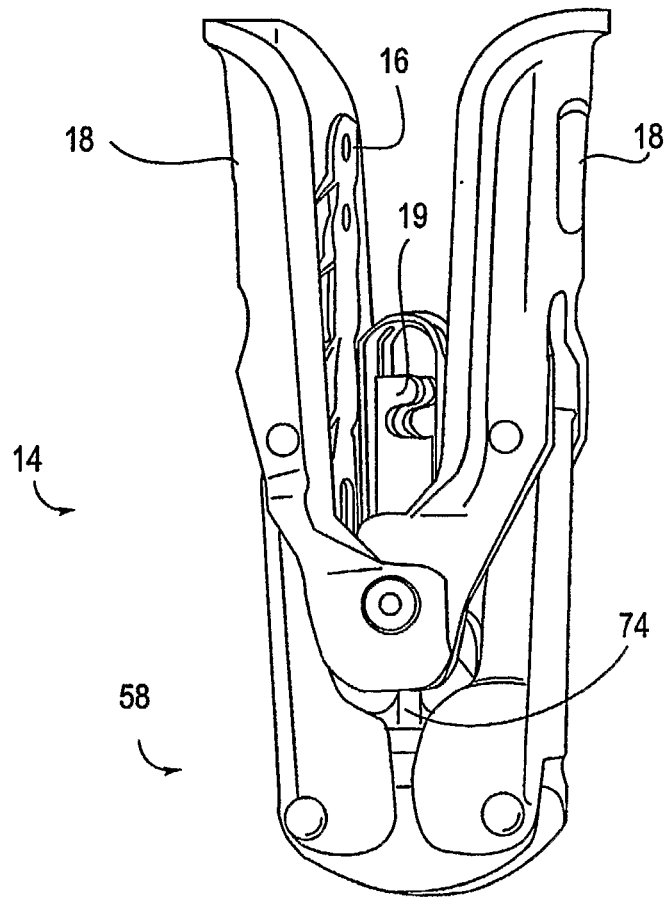

FIG. 14 illustrates a released fixation device 14 in a closed position. As shown, the coupling member 19 remains separated from the shaft 12 of the interventional tool 10 and the proximal elements 16 are deployed so that tissue (not shown) may reside between the proximal elements 16 and distal elements 18.

Instead of using a push-to-open, pull-to-close mechanism for opening and closing distal elements 18, a pull-to-open, push-to-close mechanism may also be used. For example, distal elements 18 may be coupled at their proximal ends to stud 74 rather than to coupling member 19, and legs 68 may be coupled at their proximal ends to coupling member 19 rather than to stud 74. In this example, when stud 74 is pushed distally relative to coupling member 19, distal elements 18 would close, while pulling on stud 74 proximally toward coupling member 19 would open distal elements 18.

B. Covering on Fixation Device

The fixation device 14 may optionally include a covering. The covering may assist in grasping the tissue and may later provide a surface for tissue ingrowth. Ingrowth of the surrounding tissues, such as the valve leaflets, provides stability to the device 14 as it is further anchored in place and may cover the device with native tissue, thus reducing the possibility of immunologic reactions. The covering may be comprised of any biocompatible material, such as polyethylene terephthalate, polyester, cotton, polyurethane, expanded polytetrafluoroethylene (ePTFE), silicone, or various polymers or fibers and have any suitable form, such as a fabric, mesh, textured weave, felt, looped or porous structure. Generally, the covering has a low profile so as not to interfere with delivery through an introducer sheath or with grasping and coapting of leaflets or tissue.

Figure 15A:
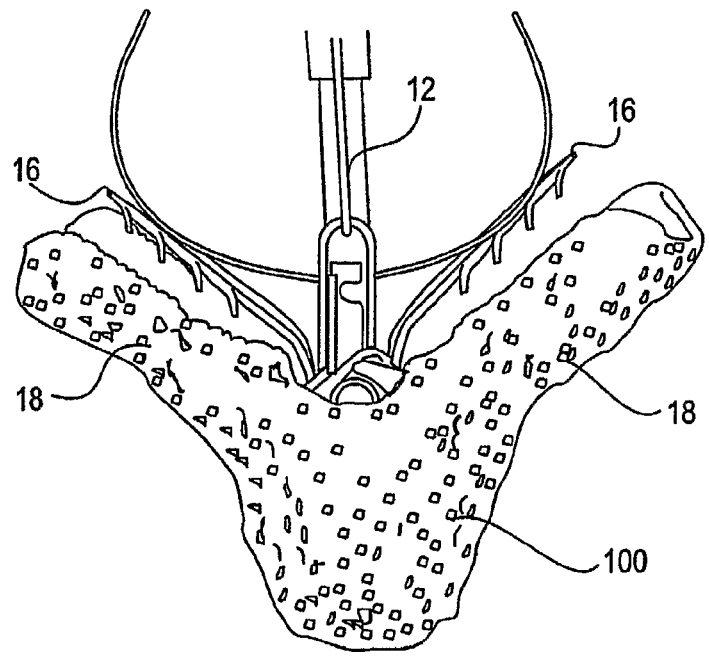
FIGS. 15A-15C illustrate a covering on the fixation device wherein the device is in various positions.
Figure 15B:
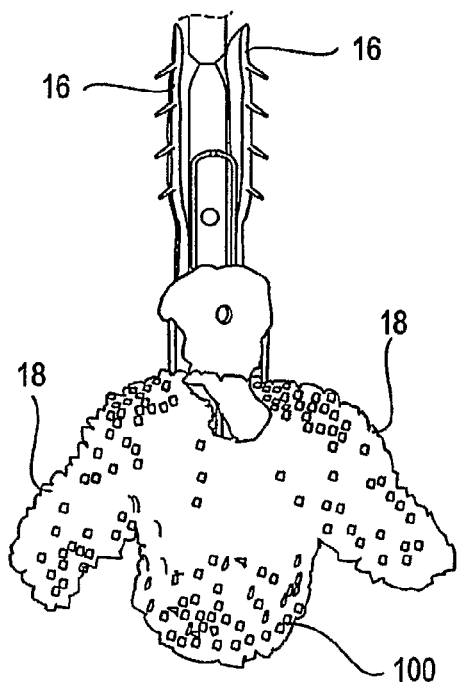
Figure 15C:
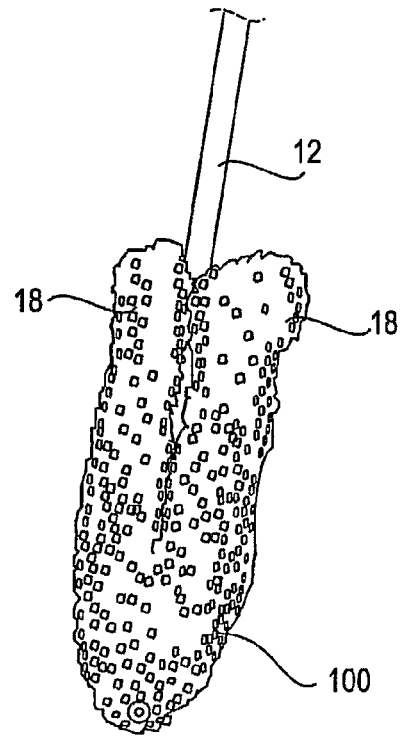

FIGS. 15A-15C illustrate a covering 100 on the fixation device 14 while the device 14 is in various positions. Additional description regarding such coverings may be found in PCT Publication No. WO 2004/103162, the disclosure of which is incorporated herein by reference in its entirety.

C. Locking Mechanism

Figure 16:
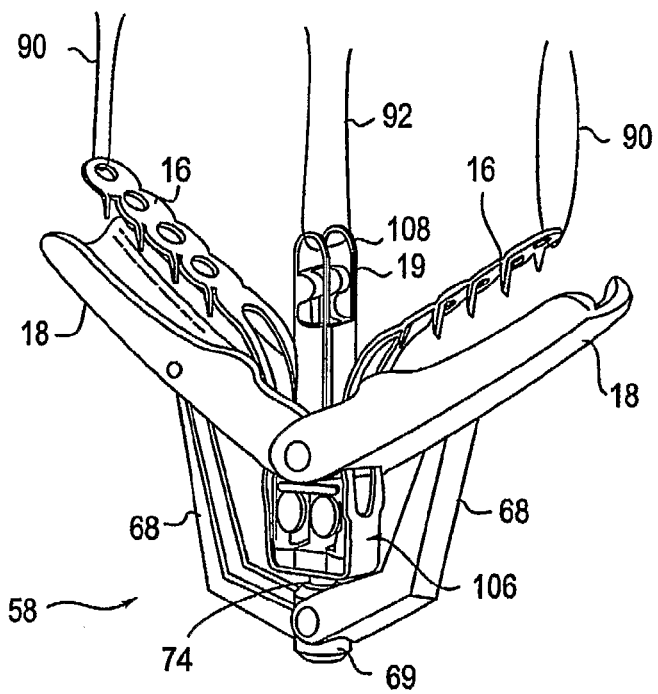
FIG. 16 illustrates a fixation device including proximal elements and a locking mechanism.

As mentioned previously, the fixation device 14 optionally includes a locking mechanism for locking the device 14 in a particular position, such as an open, closed or inverted position or any position therebetween. It may be appreciated that the locking mechanism includes an unlocking mechanism which allows the device to be both locked and unlocked. Various locking mechanisms can be used with the fixation device 14, such as those described in PCT Publication No. WO 2004/103162, which is incorporated herein by reference in its entirety. FIGS. 16-19 illustrate an exemplary locking mechanism 106. Referring to FIG. 16, the locking mechanism 106 is disposed between the coupling member 19 and the base 69 of the actuation mechanism 58. The base 69 is fixedly attached to the stud 74 which extends through the locking mechanism 106. The stud 74 is releasably attached to the actuator rod 64 which passes through the coupling member 19 and the shaft 12 of the interventional tool 10. The base 69 is also connected to the legs 68 of the actuation mechanism 58 which are in turn connected to the distal elements 18.

FIG. 16 also illustrates the proximal elements 16, which straddle the locking mechanism and join beneath the locking mechanism 106. The proximal elements 16 are shown supported by proximal element lines 90. The proximal elements 16 are raised and lowered by manipulation of the proximal element lines 90. In addition, lock lines 92 are shown connected with a release harness 108 of the locking mechanism 106. The lock lines 92 are used to lock and unlock the locking mechanism 106 as will be described below. The proximal element lines 90 and lock lines 92 may be comprised of any suitable material, typically wire, nitinol wire, cable, suture or thread, to name a few. In addition, the proximal element lines 90 and/or lock lines 92 may include a coating, such as parylene. Parylene is a vapor deposited pinhole free protective film which is conformal and biocompatible. It is inert and protects against moisture, chemicals, and electrical charge.

Figure 17:
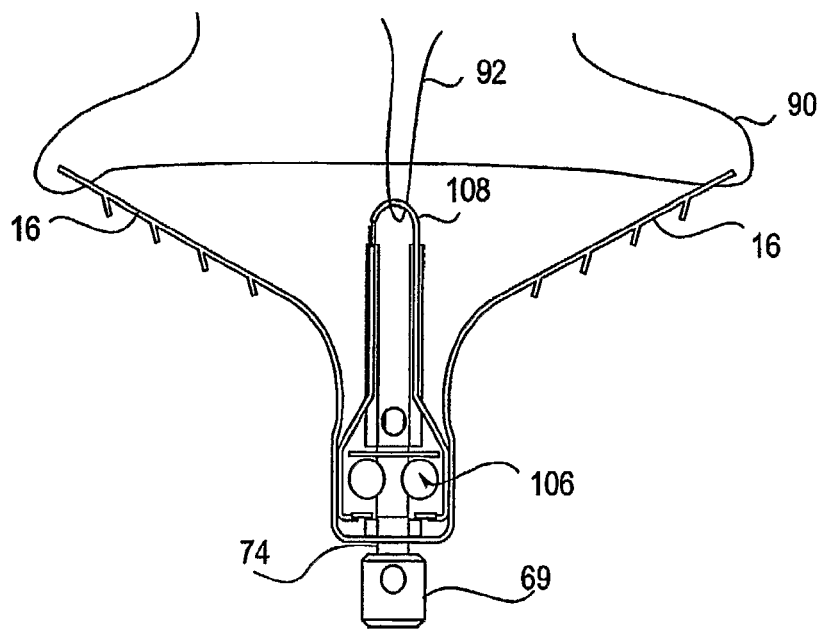
FIG. 17 provides a cross-sectional view of the locking mechanism of FIG. 16.

FIG. 17 provides a front view of the locking mechanism 106 of FIG. 16. However, here the proximal elements 16 are supported by a single proximal element line 90 which is through both of the proximal elements 16. In this arrangement both of the elements are raised and lowered simultaneously by action of a single proximal element line 90. Whether the proximal elements 16 are manipulated individually by separate proximal element lines 90 or jointly by a single proximal element line 90, the proximal element lines 90 may extend directly through openings in the proximal elements and/or through a layer or portion of a covering 100 on the proximal elements, or through a suture loop above or below a covering 100.

Figure 18:
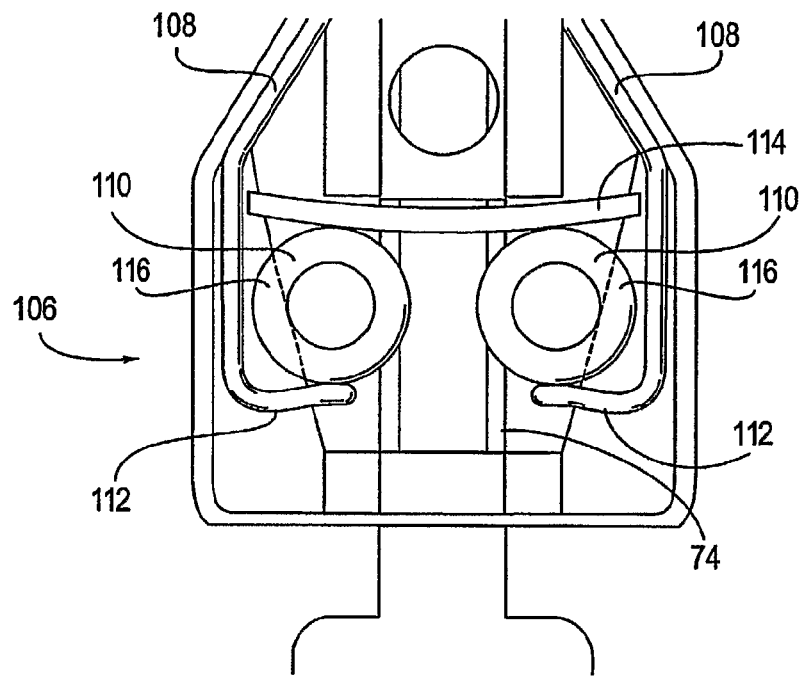
FIGS. 18-19 provide a cross-sectional view of the locking mechanism in the unlocked and locked positions respectively.
Figure 19:
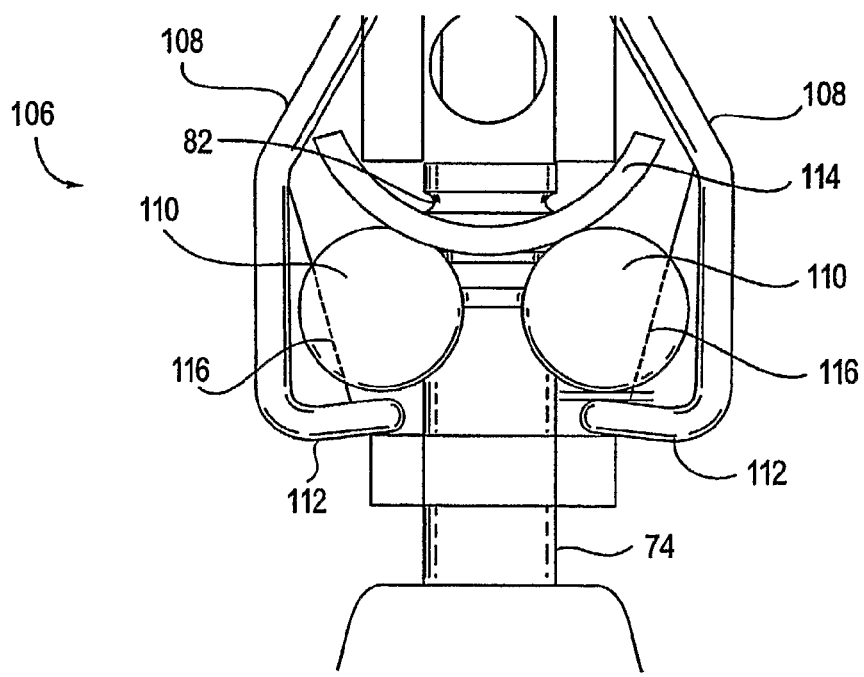

FIGS. 18-19 illustrate the locking mechanism 106 showing the locking mechanism 106 in the unlocked and locked positions respectively. Referring to FIG. 18, the locking mechanism 106 includes one or more wedging elements, such as rolling elements. In this example, the rolling elements comprise a pair of barbells 110 disposed on opposite sides of the stud 74, each barbell having a pair of generally cylindrical caps and a shaft therebetween. The barbells 110 and the stud 74 are preferably comprised of cobalt chromium or stainless steel, however any suitable material may be used. The barbells 110 are manipulated by hooked ends 112 of the release harness 108. When an upwards force is applied to the harness 108 by the lock line 92 (illustrated in FIG. 16), the hooked ends 112 raise the barbells 110 against a spring 114, as shown in FIG. 18. This draws the barbells 110 up along a sidewall or sloping surface 116 which unwedges the barbells 110 from against the stud 74. In this position, the stud 74 is free to move. Thus, when the lock line 92 raises or lifts the harness 108, the locking mechanism 106 is in an unlocked position wherein the stud 74 is free to move the actuation mechanism 58 and therefore the distal elements 18 to any desired position. Release of the harness 108 by the lock line 92 transitions the locking mechanism 106 to a locked position, illustrated in FIG. 19. By releasing the upwards force on the barbells 110 by the hooked ends 112, the spring 114 forces the barbells 110 downwards and wedges the barbells 110 between the sloping surface 116 and the stud 74. This restricts motion of the stud 74, which in turn locks the actuation mechanism 58 and therefore distal elements 18 in place. In addition, the stud 74 may include one or more grooves 82 or indentations which receive the barbells 110. This may provide more rapid and positive locking by causing the barbells 110 to settle in a definite position, increase the stability of the locking feature by further preventing movement of the barbells 110, as well as providing a tangible indication to the user that the barbell has reached a locking position. In addition, the grooves 82 may be used to indicate the relative position of the distal elements 18, particularly the distance between the distal elements 18. For example, each groove 82 may be positioned to correspond with a 0.5 or 1.0 mm decrease in distance between the distal elements 18. As the stud 74 is moved, the barbells 110 will contact the grooves 82; by counting the number of grooves 82 that are felt as the stud 74 is moved, the user can determine the distance between the distal elements 18 and can provide the desired degree of coaptation based upon leaflet thickness, geometry, spacing, blood flow dynamics and other factors. Thus, the grooves 82 may provide tactile feedback to the user.

The locking mechanism 106 allows the fixation device 14 to remain in an unlocked position when attached to the interventional tool 10 during grasping and repositioning and then maintain a locked position when left behind as an implant. It may be appreciated, however, that the locking mechanism 106 may be repeatedly locked and unlocked throughout the placement of the fixation device 14 if desired. Once the final placement is determined, the lock line 92 and proximal element lines 90 are removed and the fixation device is left behind.

As described herein, at a later stage, e.g., during a new endovascular procedure, the fixation device may be disabled or removed by cutting or otherwise partitioning the fixation device, or cutting the fixation device from tissue surrounding the installed device. For example, at such a later stage (e.g., weeks, months, or years after initial placement), it may no longer be practical to remove the device by unlocking the locking mechanism and disengaging the device from the leaflets (e.g., due to tissue growth around, into, and over the device).

Advantageously, such disablement or removal of the fixation device may be achieved through an endovascular procedure, without requiring open heart access.

D. Overview of Delivery Device

Figure 20:
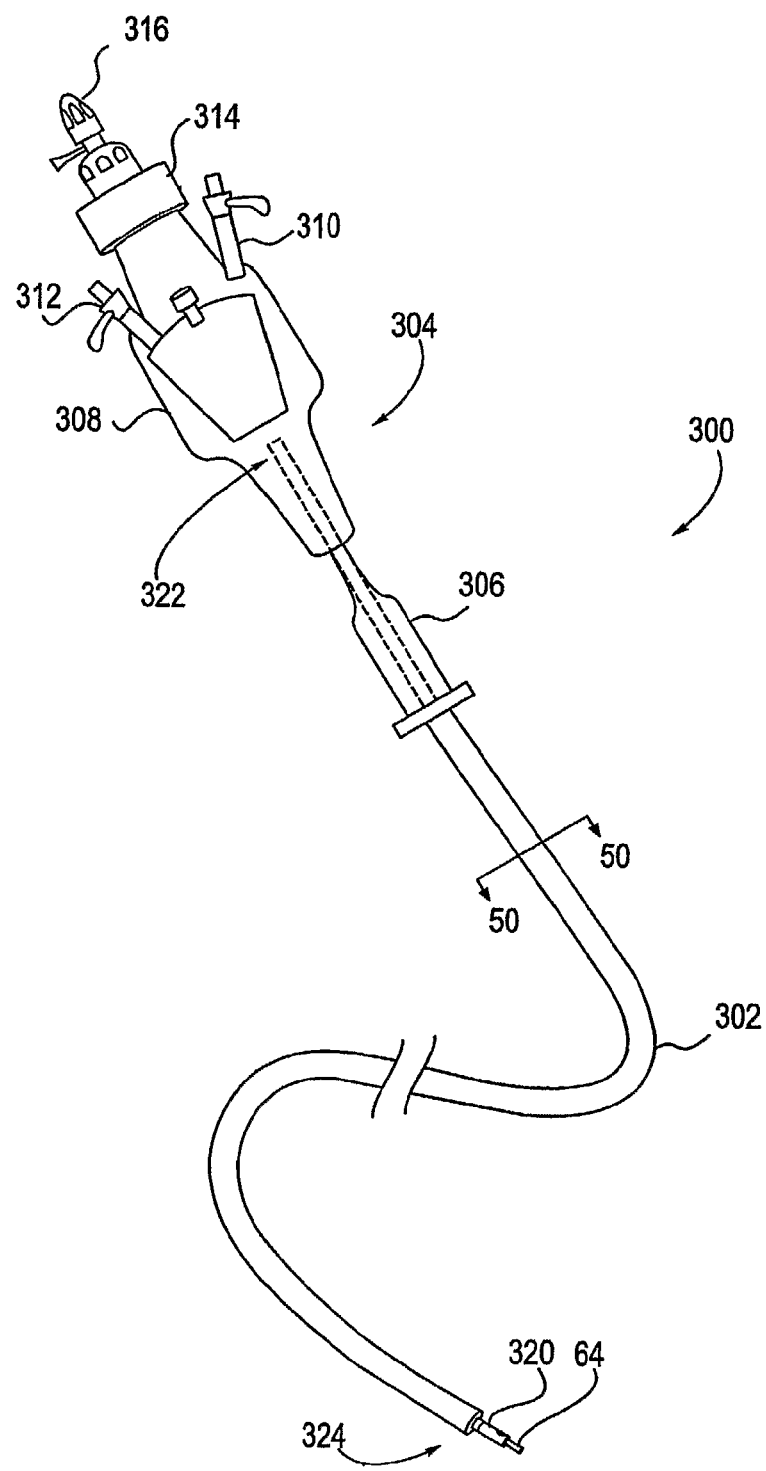
FIG. 20 illustrates a perspective view of an embodiment of a delivery catheter for a fixation device.

FIG. 20 provides a perspective view of an embodiment of a delivery device or delivery catheter 300 which may be used to introduce and position a fixation device as described above. The delivery catheter 300 includes a shaft 302, having a proximal end 322 and a distal end 324, and a handle 304 attached to the proximal end 322. A fixation device (not shown) is removably coupleable to the distal end 324 for delivery to a site within the body, typically for endovascular delivery to the mitral valve. Thus, extending from the distal end 324 is a coupling structure 320 for coupling with a fixation device. Also extending from the distal end 324 is an actuator rod 64. The actuator rod 64 is connectable with the fixation device and acts to manipulate the fixation device, typically opening and closing the distal elements. Such coupling to a fixation device is illustrated in FIG. 21.

The device may comprise a pair of distal elements and a pair of gripping elements as described herein. For example, each distal element and each gripping element may have a first end and a free end opposite the first end, the first ends of all of these elements being movably coupled together such that one distal element and one gripping element of the fixation device may be attached to the anterior leaflet, and one distal element and one gripping element of the fixation device may be attached to the posterior leaflet, and further comprising a locking mechanism which locks at least the distal elements in place, wherein the locking mechanism includes a release harness, wherein applying tension to the release harness unlocks the locking mechanism. In an embodiment, the release harness may from at or near the first ends of the distal and gripping elements at one end to past the free ends of the distal and gripping elements at an opposite end. Such a configuration advantageously makes it easier for a practitioner to access and engage a lock line 92 with the release harness. Such an embodiment is shown and described below in conjunction with FIG. 38.

Figure 21:
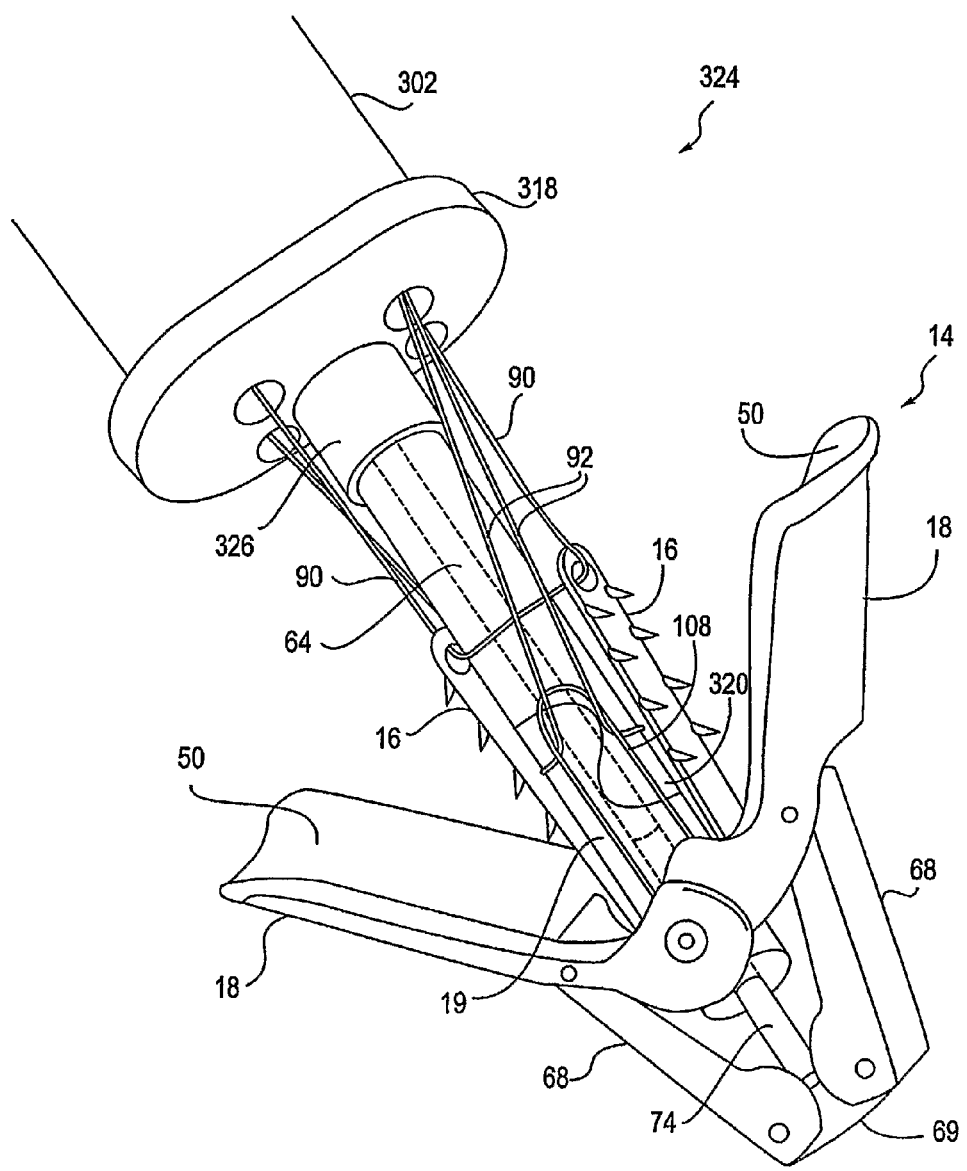
FIG. 21 illustrates an embodiment of a fixation device coupled to the distal end of a delivery catheter.

FIG. 21 illustrates an embodiment of a fixation device 14 coupled to the distal end 324 of the delivery catheter 300. The shaft 302 is shown having a nose 318 near its distal end 324. In this embodiment, the nose 318 has a flanged shape. Such a flanged shape prevents the nose 318 from being retracted into a guiding catheter or introducer as will be discussed in later sections. However, it may be appreciated that the nose 318 may have any shape including bullet, rounded, blunt or pointed, to name a few. Extending from the nose 318 is a compression coil 326 through which the coupling structure 320 and actuator rod 64 pass. The actuator rod 64 is coupleable, as shown, with the stud 74 of the fixation device 14. Such coupling is illustrated in FIG. 22.

Figure 22:
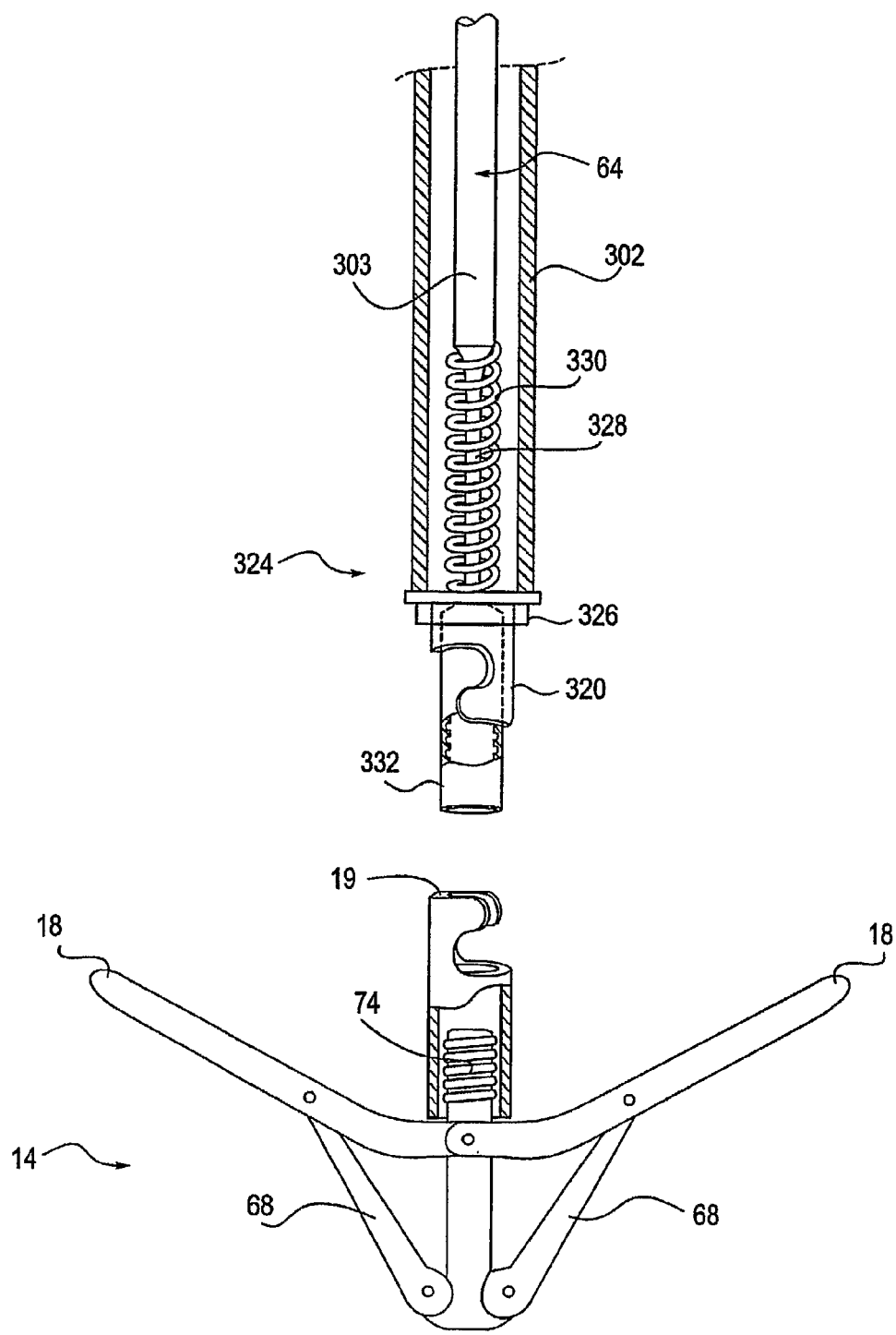
FIG. 22 illustrates a portion of the shaft of a delivery catheter and a fixation device which is coupleable with the catheter.

FIG. 22 illustrates a portion of the shaft 302 of the delivery catheter 300 and a fixation device 14 which is coupleable with the catheter 300. Passing through the shaft 302 is the actuator rod 64. In this embodiment, the actuator rod 64 comprises a proximal extremity 303 and a distal extremity 328, the distal extremity 328 of which is surrounded by a coil 330. The proximal extremity 303 is typically comprised of a material such as stainless steel, nitinol, or Elgiloy®, to name a few, and may have a diameter in the range of 0.010 in. to 0.040 in., preferably 0.020 in. to 0.030 in., more preferably 0.025 in., and a length in the range of 48 to 72 in. The distal extremity 328 may be tapered, is typically comprised of stainless steel, nitinol, or Elgiloy®, to name a few, and may have a diameter in the range of 0.011 to 0.025 in and a length in the range of 4 to 12 in. Such narrowing increases flexibility of the distal end 324 of the actuator rod 64. The actuator rod 64 further comprises a joiner 332 which is attached to the distal extremity 328. The joiner 332 is removably attachable with stud 74 of the fixation device 14. In this embodiment, the joiner 332 has internal threads which mate with external threads on the stud 74 of the fixation device 14. As described previously, the stud 74 is connected with the distal elements 18 so that advancement and retraction of the stud 74, by means of the actuator rod 64, manipulates the distal elements. Likewise, the coupling member 19 of the fixation device 14 mates with the coupling structure 320 of the catheter 300. Thus, the coupling member 19 and coupling structure 320 may function as previously described in relation to FIGS. 6A-6B.

Referring back to FIG. 21, the fixation device 14 may also include a locking mechanism which includes a release harness 108, as previously described in relation to FIGS. 16-19. Lock lines 92 are connected with the release harness 108 to lock and unlock the locking mechanism 106 as previously described. The lock lines 92 extend through the shaft 302 of the delivery catheter 300 and may connect with the release harness 108 in various arrangements as will be illustrated in later sections. Similarly, proximal element lines 90 extend through the shaft 302 of the delivery catheter 300 and connect with the proximal elements 16. The proximal elements 16 are raised and lowered by manipulation of the proximal element lines 90 as previously described. The proximal element lines 90 may connect with the proximal elements 16 in various arrangements.

Referring back to FIG. 20, the handle 304 attached to the proximal end 322 of the shaft 302 is used to manipulate the coupled fixation device 14 and to optionally decouple the fixation device 14 for permanent implantation. As described, the fixation device 14 is primarily manipulated by the actuator rod 64, proximal element lines 90 and lock lines 92. The actuator rod 64 manipulates the distal elements 18, the proximal element lines 90 manipulate the proximal elements 16 and the lock lines 92 manipulate the locking mechanism. The actuator rod 64 may be translated (extended or retracted) to manipulate the distal elements 18. This is achieved with the use of the actuator rod control 314 which will be described in later sections. The actuator rod 64 may also be rotated to engage or disengage the threaded joiner with the threaded stud 74. This is achieved with the use of the actuator rod handle 316 which will also be described in later sections. Further, the proximal element lines 90 may be extended, retracted, loaded with various amounts of tension or removed with the use of the proximal element line handle 312. The lock lines 92 may be extended, retracted, loaded with various amounts of tension or removed with the use of the lock line handle 310. The actuator rod handle 316, actuator rod control 314, proximal element line handle 312 and lock line handle 310 are all joined with a main body 308 within which the actuator rod 64, proximal element lines 90 and lock lines 92 are guided into the shaft 302. The handle 304 further includes a support base 306 connected with the main body 308. The main body 308 is slideable along the support base 306 to provide translation of the shaft 302. Further, the main body 308 is rotatable around the support base 306 to rotate the shaft.

E. Delivery Catheter Shaft

Figure 23:
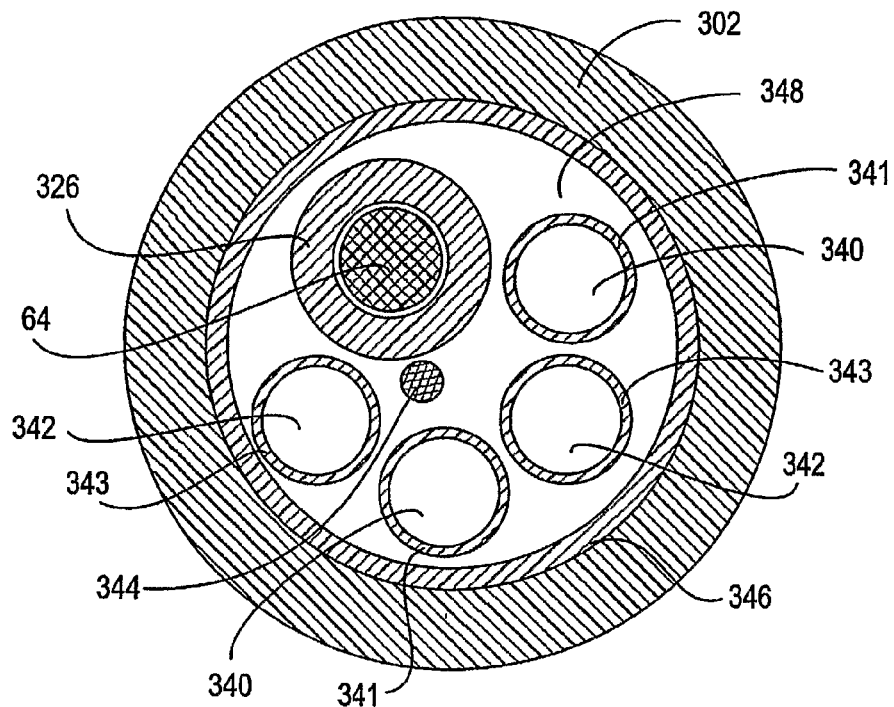
FIG. 23 is a cross-sectional view of the shaft of a delivery catheter.

FIG. 23 illustrates a cross-sectional view of the delivery catheter shaft 302 of FIG. 20. The shaft 302 has a tubular shape with inner lumen 348 and is comprised of a material which provides hoop strength while maintaining flexibility and kink resistance, such as a braided laminated material. Such material may include stainless steel braided or coiled wire embedded in a polymer such as polyurethane, polyester, Pebax, Grilamid TR55, and AESNO to name a few. To provide further support and hoop strength, a support coil 346 is disposed within the lumen 348 of shaft 302 as illustrated in FIG. 23.

Additional description regarding such a catheter may be found in PCT Publication No. WO 2004/103162, the disclosure of which is incorporated herein by reference in its entirety.

In addition, at least one lock line shaft 341 having a tubular shape may be present having a lock line lumen 340 through which lock lines 92 pass between the lock line handle 310 and the locking mechanism 106. The lock line shaft 341 extends through lumen 348 from the proximal end 322 to the distal end 324 of the shaft 302. Therefore, the lock line shaft 341 typically has a length in the range of 48 to 60 in., an inner diameter in the range of 0.016 to 0.030 in., and an outer diameter in the range of 0.018 to 0.034 in. The lock line shaft 341 may be comprised of a 304V stainless steel coil, however, other structures or materials may be used which provide kink resistance and compression strength.

Similarly, at least one proximal element line shaft 343 having a tubular shape may be present having a proximal element line lumen 342. Proximal element lines 90 pass through this lumen 342 between the proximal element line handle 312 and the proximal elements 16. Thus, the proximal element line shaft 343 extends through lumen 348 from the proximal end 322 to the distal end 324 of the shaft 302. Therefore, the proximal element line shaft 343 typically has a length in the range of 48 to 60 in., an inner diameter in the range of 0.016 to 0.030 in., and an outer diameter in the range of 0.018 to 0.034 in. The proximal element line shaft 343 may be comprised of a 304V stainless steel coil, however, other structures or materials may be used which provide kink resistance and compression strength.

It may be appreciated, however, that alternate shaft 302 designs may also be used. For instance, other shaft designs can be found in PCT Publication No. WO 2004/103162.

F. Lock Line Arrangements

Figure 24:
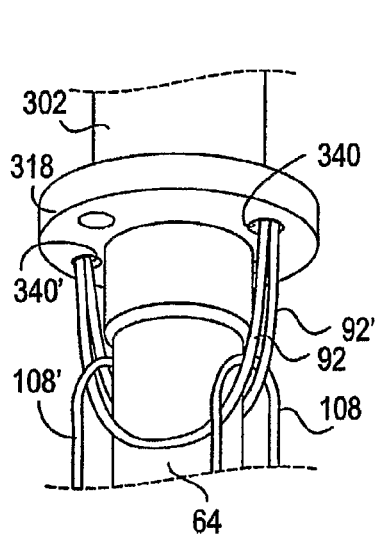
FIG. 24 illustrates various arrangements of lock lines engaging release harnesses of a locking mechanism.

As mentioned previously, when lock lines 92 are present, the lines 92 pass through at least one lock line lumen 340 between the lock line handle 310 and the locking mechanism 106. The lock lines 92 engage the release harnesses 108 of the locking mechanism 106 to lock and unlock the locking mechanism 106 as previously described. The lock lines 92 may engage the release harnesses 108 in various arrangements, examples of which are illustrated in FIG. 24. The two lock line lumens 340 are present within the shaft 302 of the delivery catheter 300 terminating at the nose 318. The lumens 340 are disposed on alternate sides of the actuator rod 64 so that each lumen 340 is directed toward a release harness 108. FIG. 24 illustrates an arrangement wherein two lock lines 92, 92' pass through a single lock line lumen 340 and are threaded through a release harness 108 on one side of the actuator rod 64 (the actuator rod 64 is shown without surrounding housing such as coupling structure, for clarity). The lock lines 92, 92' are then separated so that each lock line passes on an opposite side of the actuator rod 64. The lock lines 92, 92' then pass through the release harness 108' on the opposite side of the actuator rod 64 and continue together passing through a another single lock line lumen 340'. This lock line arrangement is the same arrangement illustrated in FIG. 21. Alternate lock line arrangements are possible, some of which can be found in PCT Publication No. WO 2004/103162, the disclosure of which is incorporated herein by reference in its entirety It may be appreciated that a variety of lock line arrangements may be used and are not limited to the arrangements illustrated and described above. The various arrangements allow the harnesses 108 to be manipulated independently or jointly, allow various amounts of tension to be applied and vary the force required for removal of the lock lines when the fixation device is to be left behind. For example, a single lock line passing through one or two lumens may be connected to both release harnesses for simultaneous application of tension.

G. Proximal Element Line Arrangements

Figure 25:
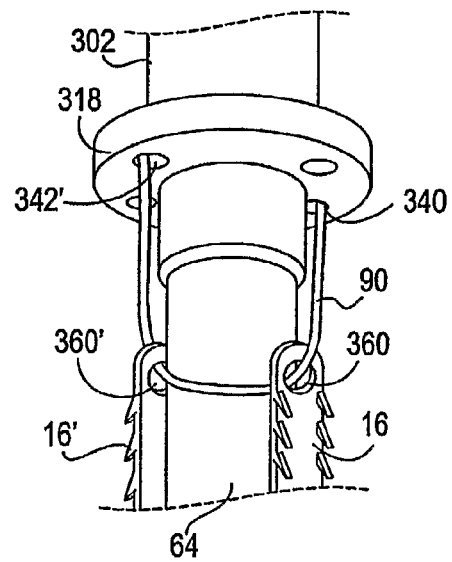
FIG. 25 illustrates various arrangements of proximal element lines engaging proximal elements of a fixation device.

As mentioned previously, when proximal element lines 90 are present, the lines 90 pass through at least one proximal element line lumen 342 between the proximal element line handle 312 and at least one proximal element 16. The proximal element lines 90 engage the proximal elements 16 to raise or lower the element 16 as previously described. The proximal element lines 90 may engage the proximal elements 16 in various arrangements, an example of which is illustrated in FIG. 25. The two proximal element line lumens 342 are present within the shaft 302 of the delivery catheter 300 terminating at the nose 318. The lumens 342 are disposed on alternate sides of the actuator rod 64 (the actuator rod 64 is shown without surrounding housing such as coupling structure, for clarity) so that each lumen 342 is directed toward a proximal element 16.

FIG. 25 illustrates an arrangement wherein one proximal element line 90 passes through a single proximal element line lumen 342. The proximal element line 90 is threaded through an eyelet 360 of a proximal element 16 on one side of the actuator rod 64, passes over the actuator rod 64 and is threaded through an eyelet 360' of another proximal element 16' on the other side of the actuator rod 64. The proximal element line 90 then passes through another single proximal element line lumen 342'. This proximal element line arrangement is the same arrangement illustrated in FIG. 21.

It may be appreciated that a variety of proximal element line arrangements may be used and are not limited to the arrangements illustrated and described above. For instance, and not by way of limitation, some alternate element line arrangements can be found in PCT Publication No. WO 2004/103162, the disclosure of which is incorporated herein by reference in its entirety. The various arrangements allow the proximal elements to be manipulated independently or jointly, allow various amounts of tension to be applied and vary the force required for removal of the proximal element lines when the fixation device is to be left behind. For example, a single proximal element line passing through one or two lumens in shaft 302 may be used for simultaneous actuation of both proximal elements.

H. Handle

Figure 26:
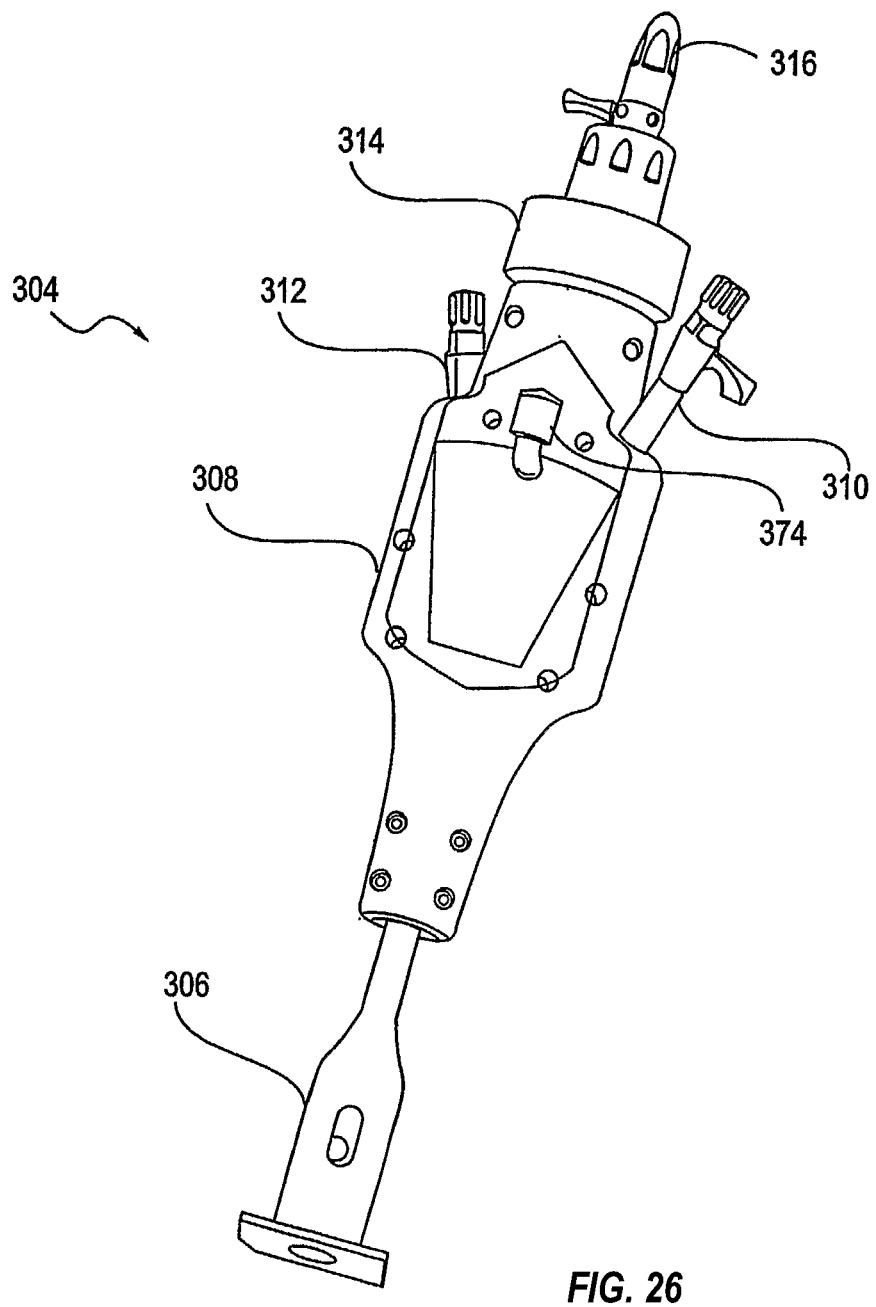
FIG. 26 illustrates a handle of a delivery catheter.

FIG. 26 illustrates a handle 304 of the delivery catheter 300. As mentioned previously, the actuator rod handle 316, actuator rod control 314, proximal element line handle 312 and lock line handle 310 are all joined with the main body 318. The handle 304 further includes a support base 306 connected with the main body 308. The main body 308 is slideable along the support base 306 to provide translation of the shaft 302 and the main body 308 is rotateable around the support base 306 to rotate the shaft.

It may be appreciated, that alternate handle 304 designs may also be used. For instance, further disclosure regarding handles can be found in PCT Publication No. WO 2004/103162, the disclosure of which is incorporated herein by reference in its entirety. For example, the handle may be designed to permit the manipulation of the lock lines and proximal element lines with the handle 304 or additional or different handles. Similarly, the handle may be designed to permit the manipulation of the actuator rod 64.

I. Placement

To gain access to the mitral valve from the atrial side, an outer guide catheter may be tracked over a dilator and guidewire from a puncture in the femoral vein, through the inferior versa cava and into the right atrium. The outer guide catheter may be punctured through a fossa in the interatrial septum, into the left atrium. The outer guide catheter is then advanced through the fossa and curved by the primary curve so that the distal end is directed over the mitral valve. It may be appreciated that this approach serves merely as an example and other approaches may be used, such as through the jugular vein, femoral artery, port access or direct access, to name a few. For example, access to the heart may be accomplished through a thoracotomy or similar procedure involving, for example, trans-apical access to the left ventricle. Positioning of the distal end over the mitral valve may be accomplished by precurvature of the outer guide catheter, wherein the catheter assumes this position when the dilator and guidewire are retracted, and/or by steering of the outer guide catheter to the desired position. Any of the above described endovascular access procedures may similarly be used when disabling or removing a previously installed fixation device.

An inner guide catheter is advanced through the central lumen of the outer guide catheter and the distal end is positioned so that the central lumen is directed toward the target tissue, the mitral valve MV. In particular, the central lumen is to be directed toward a specific area of the mitral valve, such as toward the opening or openings between the valve leaflets or a device implanted in the mitral valve.

To gain access to the mitral valve from the ventricular side, an outer guide catheter may be tracked over a dilator and guidewire from a puncture in the femoral artery, through the aorta and into the left ventricle. The outer guide catheter is then advanced through the left ventricle so that the distal end is directed under the mitral valve. It may be appreciated that this approach serves merely as an example and other approaches may be used, such as through the jugular vein, femoral vein, port access or direct access, to name a few. For example, access to the heart may be accomplished through a thoracotomy or similar procedure involving, for example, trans-apical access to the left ventricle. Positioning of the distal end under the mitral valve may be accomplished by precurvature of the outer guide catheter, wherein the catheter assumes this position when the dilator and guidewire are retracted, and/or by steering of the outer guide catheter to the desired position. Any of the above described endovascular access procedures may similarly be used when disabling or removing a previously installed fixation device.

An inner guide catheter is advanced through the central lumen of the outer guide catheter and the distal end is positioned so that the central lumen is directed toward the target tissue, the mitral valve MV. In particular, the central lumen is to be directed toward a specific area of the mitral valve, such as toward the opening between the valve leaflets.

The specific features of the fixation device 14 described above and its method of implantation are merely illustrative. Other fixation devices may be employed, and any such devices may be removed using the methods and apparatuses disclosed below.

III. Methods of Disabling or Removing a Mitral Valve Fixation Device

Sometimes, after installation of a fixation device in the heart, it needs to be removed or disabled. Ordinarily, this has been done during an invasive procedure such as open heart surgery. Invasive procedures such as these often have high risk of complications, however. Further, sometimes mitral valve fixation devices are installed on patients for whom open heart or more invasive procedures are otherwise unnecessary or undesirable. For these patients, and even for patients in whom open-heart surgery is used, it would be beneficial to have devices and systems specifically designed for removing or disabling fixation devices within an endovascular procedure, rather than a procedure requiring open heart access.

Minimally invasive systems, methods, and devices for removing or disabling fixation devices are disclosed herein. These minimally invasive systems, methods, and devices allow a practitioner to remove the fixation device or disable it and, optionally, then proceed to do other things in the heart, without necessarily requiring open heart access or other more invasive procedures. Such systems, methods, and devices are configured to be effective even if the fixation device has been installed for weeks, months, or years, such that tissue surrounding the device may have grown over, into, or around the fixation device. As a result of such tissue growth, or for other reasons, unlocking and removal of the fixation device as described above that may be practical during the initial placement procedure may no longer be practical. The systems, methods, and devices disclosed herein may also be useful for adjusting the installation of a mitral valve fixation device after it is installed.

An embodiment of the present invention discloses systems that include various devices that may include catheters that perform various functions, and also multifunctional catheters that can perform any combination of functions. Such functions may include holding or retaining an installed fixation device; cutting or otherwise partitioning the fixation device, cutting a leaflet or leaflets; removing a fixation device; and repairing the leaflet(s). Related methods for performing such functions are also disclosed.

The devices and associated methods and systems described herein may be used in combination with imaging modalities such as x-ray, fluoroscopy, echocardiography, charge coupled device cameras, complementary metal oxide semiconductor cameras, magnetic resonance imaging, and other imaging modalities. The availability of such imaging modalities during such procedures may help practitioners visualize, for example, where the fixation devices are, how they are connected to the heart, and where to direct the various catheters and/or other devices.

A. Systems for Removing or Disabling a Fixation Device

Figure 27:
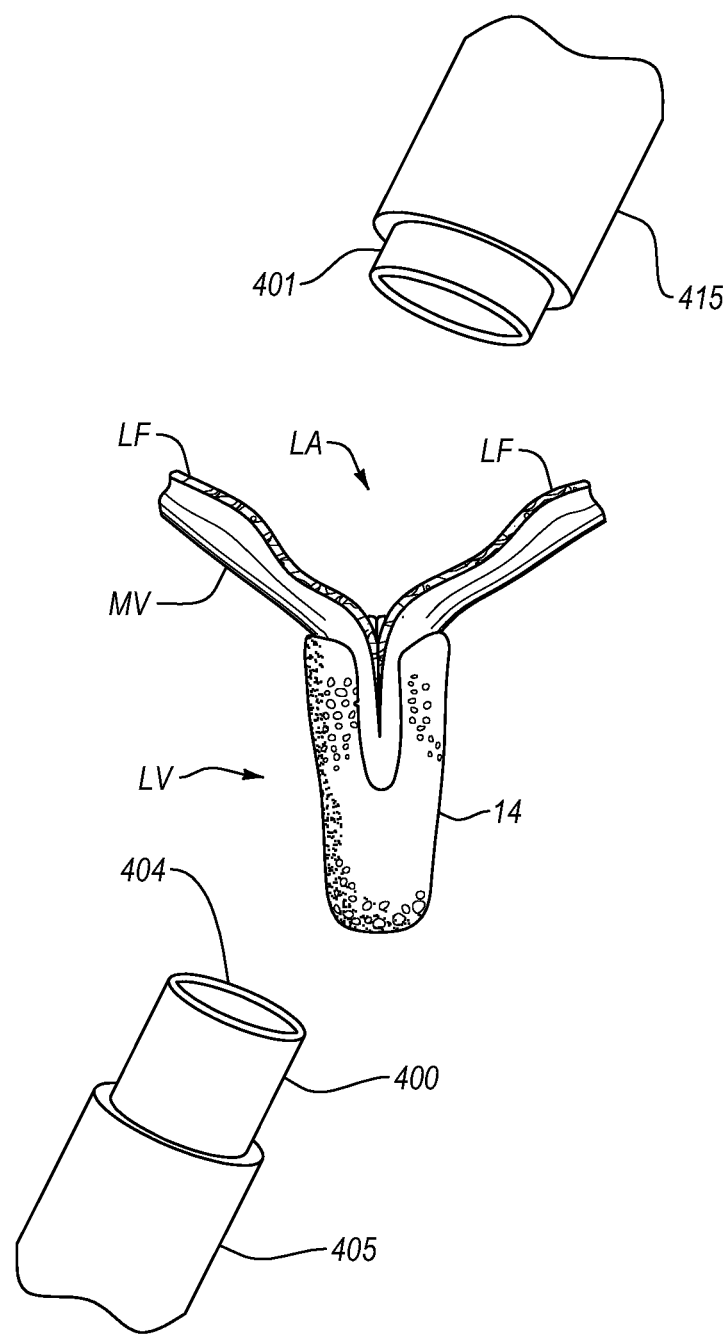
FIG. 27 illustrates a system for removing or disabling a fixation device.

FIG. 27 illustrates an exemplary fixation device 14 that may be implanted in a mitral valve MV as described above, and that needs to be disabled or removed. According to an embodiment, two inner guide catheters, catheter 400 and catheter 401 may be disposed adjacent to the installed fixation device 14 in preparation for disabling or removing the fixation device 14. Catheters 400 and 401 may advantageously be positioned in the heart following a similar endovascular deployment approach as described above. For instance, catheter 400 may be advanced into the left ventricle LV through an outer guide catheter 405, and catheter 401 may be advanced into the left atrium LA through another outer guide catheter 415. In some embodiments, both catheters 400 and 401 may be positioned in the heart on the same side of the mitral valve MV (either both in the left ventricle LV or both in the left atrium LA). In some embodiments, only one of catheters 400 or 401 may be used. In other embodiments, more than two catheters may be used. In some embodiments, one or more of the catheters 400 or 401 may initially be advanced into the left atrium LA, pass through one of the two orifices O (shown in FIG. 35), and approach the fixation device 14 from the left ventricle LV. Similarly, one or more of the catheters 400 or 401 may initially be advanced into the LV, pass through one of the two orifices O (shown in FIG. 35), and approach the fixation device 14 from the left atrium LA. It will be appreciated that any device or method described in relation to catheter 400 may also or instead be associated with catheter 401. Similarly, any device or method described in relation to catheter 401 may also or instead be associated with catheter 400.

In one embodiment, catheter 400 may be associated with a capture assembly 402, while catheter 401 may be associated with a cutter assembly 403. The capture assembly 402 may be mounted on or in catheter 400, and may be advanced out of outer guide catheter 405 by e.g., advancing catheter 400 or retracting guide catheter 405.

FIG. 28 illustrates an exemplary capture assembly 402. Capture assembly may include an elongate member 406 which extends out the distal end of catheter 400. In an embodiment, elongate member 406 may extend from the distal end 404 of the catheter 400 to a proximal handle manipulable by the practitioner. The elongate member 406 may be made of metal, plastic, or any suitable material, e.g., such as those described herein (e.g., cobalt-chromium alloys, stainless steel, nickel-titanium, Elgiloy®, etc. The elongate member 406 may be used to control a capturing mechanism 407 in the capture assembly 402. As illustrated in FIG. 28, the capturing mechanism 407 may comprise a lasso-type structure 408. Other types of capturing mechanisms 407 may include, but are not limited to, for example, sheaths, conduits, expandable baskets, vacuums, magnets, vices, and clamps. Such capturing mechanisms, including lasso-type structure 408 are examples of retaining means, as they serve to retain the fixation device 14 within their control.

The lasso-type capturing mechanism 408 may include a portion of wire or cord 409 which is designed to assume an oval or ring-shaped structure 410, at least when it is deployed outside the outer guide catheter 405, and in which the size of the oval or ring-shaped structure can be adjusted. The portion of wire or cord 409 may be designed to be able to assume another shape when it is inside of the outer guide catheter 405 (e.g., it may comprise a superelastic nickel-titanium or other very flexible material). This may allow the lasso-type capturing mechanism 408 to be delivered in an outer guide catheter 405 with a smaller diameter than the diameter (or diameters) of the deployed ring or oval-shaped structure 410.

The angle 411 between the plane on which the ring or oval-shaped structure 410 lies and the distal-most portion of the elongate member 406, when the lasso-type capturing mechanism 408 is outside of the outer guide catheter 405, may be varied depending on the direction from which the capture assembly 402 is intended to approach the fixation device 14. For example, if the capture assembly 402 is intended to approach the fixation device 14 from directly below the fixation device 14 as it is installed in the heart, the angle 411 may be approximately 90°, as illustrated. In other embodiments, the angle may be about 45°, about 135°, or from about 45° to 135°. Other angles may also be provided, depending on the alignment characteristics of the procedure relative to the fixation device to be grasped therein. Preferably, the capture assembly 402 may be designed such that when the lasso-type capturing mechanism 408 is located in the outer guide catheter 405, the angle 411 between the plane on which the ring or oval-shaped structure 410 lies and the catheters 400 and 405 may be or approximate 0° or 180°. This may also reduce the size of the outer guide catheter 405 needed to deliver the capture assembly 402.

The lasso-type capturing mechanism 408 may be designed such that the portion of wire or cord 409 which is designed to assume an oval or ring-shaped structure 410 may be increased or decreased by controlling the elongate member 406 at the proximal end of the catheter. This allows for the diameter or circumference of the oval or ring-shaped structure 410 to be changed as appropriate once the lasso-type capturing mechanism 408 is advanced out of the outer guide catheter 405 in the heart. When the portion of wire or cord 409 is reduced, a part of the portion of wire or cord 409 may become part of the elongate member 406. Similarly, when the portion of wire or cord 409 is increased, a part of the elongate member 406 may become part of the portion of wire or cord 409.

The oval or ring-shaped structure 410 of wire 409 may be encircled by a helical loop 412. Helical loop 412 may be formed of a wire having a smaller diameter than that of wire 409. The helical loop 412 may wrap around the oval or ring-shaped structure 410. This helical loop 412 may be made of metal, plastic, or other suitable material. Helical loop 412 may help the oval or ring-shaped structure 410 retain an approximately circular or oval shape and may also improve the ability of the lasso-type capturing mechanism 408 to grip the fixation device 14 and any tissue surrounding the fixation device 14.

The helical loop 412 may be expandable or compressible so that the ability of the oval or ring-shaped structure 410 to be increased or decreased in circumference is not inhibited by the presence of helical loop 412.

The oval or ring-shaped structure 410 is designed to be large enough or able to be enlarged such that it can encircle the fixation device 14, or a portion thereof, and any tissue grown into or around that portion of the fixation device 14 to be captured. This may be achieved from the ventricle LV side of the mitral valve MV. When the oval or ring-shaped structure 410 is placed such that it encircles the fixation device 14, or a portion of it, the elongate member 406 may be controlled in order to decrease the diameter of the oval or ring-shaped structure 410. It may be beneficial for the diameter of the oval or ring-shaped structure 410 to be decreased once the oval or ring-shaped structure 410 is placed at a desired location around the fixation device 14, in order to allow for the capture assembly 402 to provide a firm hold on the fixation device 14.

In one embodiment, the capture assembly 402 includes a loop control element 414 that is located near the distal end of elongate member 406, e.g., at or near the connection of the portion of wire or cord 409 and elongate member 406. Loop control element 414 may include a tunnel formed therethrough, allowing the elongate member 406 to be passed through the loop control element 414. The loop control element 414 may further be slidable along the elongate member 406, such that sliding the loop control element 414 distally tightens or narrows the ring 410, and sliding loop control element 414 proximally loosens or widens ring 410. Manipulation of loop control element 414 may be achieved from the proximal end of the catheter 400 (e.g., through a push rod or similar mechanism), so as to change the length of the portion of wire or cord 409, so as to loosen or tighten ring 410. As such, loop control element 414 is an example of means for increasing or decreasing the size of the ring 410.

As noted above, the catheter 401 may be associated with a cutter assembly 403. After the fixation device 14 is stabilized and held by the capture assembly 402, the cutter assembly 403 may be used to cut one or both leaflets LF in order to remove or disable the fixation device 14. In some embodiments, the cutter assembly 403 may also be used to cut the fixation device 14 into two or more pieces, e.g., cutting device 14 into two pieces, and leaving one piece attached to each leaflet LF. While the device remains attached to the mitral valve (one portion attached to each leaflet), the fixation device may be thus disabled.

An exemplary cutter assembly 403 is illustrated in FIG. 29. The cutter assembly 403 is associated with catheter 401 and is designed so that it can be delivered to near the mitral valve MV inside of an outer guide catheter 415. In some embodiments, the cutter assembly 403 includes an elongate member 416 which may extend out the distal end of catheter 401 (e.g., it may extend the entire length of the catheter 401 to the proximal handle. The elongate member 416 may be made of metal, plastic, or any suitable material. The catheter 401 may be used to advance and retract the cutter assembly 403 within the outer guide catheter 415 and out the distal end 417 of the outer guide catheter 415. The elongate member 416 may be used to control a cutting mechanism 418 in the cutter assembly 403. As illustrated in FIG. 29, the cutting mechanism 418 may include a blade 420. Such a blade 420 is an example of means for cutting. Other exemplary cutting means may include, for example, radiofrequency energy emitters, lasers, other energy emitters (e.g., electrical current, etc.) that may serve to cut and/or cauterize tissue or the fixation device, and variously configured blades (e.g., an annular blade, rotating tip or blade, etc.). The cutter assembly 403 may be large enough that the entire fixation device may fit into the lumen 434 of the catheter 401.

The blade 420 may be mounted in the cutter assembly 403. The blade 420 is mounted so that the sharp edge 421 of the blade 420 faces the distal end 417 of the outer guide catheter 415 when the cutter assembly 403 is inside of the catheter 415. Another cutting board of the cutter assembly 403 may be located distal to the blade 420. The cutting board 422 may be approximately disk-shaped, and the cutting board 422 may be attached to the rest of the cutter assembly 403 by the elongate member 416. Controlling the elongate member 416 from the proximal end of the catheter 401 may permit the cutting board 422 to be moved toward and away from the blade 420. The blade 420 and cutting board 422 may function together to cut tissue that is brought between the blade 420 and cutting board 422. As the cutting board 422 is drawn toward the blade 420, the blade 420 will cut through tissue located between the sharp edge 421 of the blade 420 and the cutting board 422, until the sharp edge 421 of the blade 420 comes into contact with the cutting board 422. Depending on the size of the area to be cut, this cutting process may be repeated.

By controlling the catheter 401 from the proximal end of the catheter 401, the cutter mechanism 418 may be advanced into the left atrium LA until the cutting board 422 and blade 420 are located adjacent to tissue to be cut. This may entail lowering the cutter mechanism 418 partially into one of the orifices of the double orifice structure formed by the implantation of the fixation device 14.

The cutter assembly 430 may approach the fixation device 14 from the left atrium LA, or from the left ventricle LV.

In order to disable the fixation device 14, one mitral valve leaflet LF could be cut adjacent to the free end 54 of one of the distal elements 18 of the fixation device 14 in order to separate that mitral valve leaflet LF from that distal element 18 and its associated proximal element 16. (For the structure of the fixation device 14, see, e.g., FIG. 7.) The fixation device 14 may also be separated from both leaflets LF for removal by cutting both leaflets LF adjacent to each free end 54 of the distal elements 14.

The sharp edge 421 of the blade 420 may or may not be parallel to the distal edge 423 of the catheter 401. The sharp edge 421 of the blade 420 may be linear, or it may be annular, following all or a portion of the arc associated with the inside circumference of catheter 401, or another appropriate shape.

The cutting board 422 may be made of a material which allows for the blade 420 to, after cutting through tissue, slightly cut into the cutting board 422. However, the cutting board 422 should be made of a hard enough material that the blade 420 does not slice all of the way through the cutting board 422. It may be preferable to have the cutting board 422 comprise two different materials. At the most distal end 424 of the cutting board, a harder material may be used, and on the surface 425 which the blade 420 cuts against, a softer material may be used. If the sharp edge 421 of the blade 420 is not parallel to the distal edge 423 of the catheter, it may be desirable to have the surface 425 designed so that the connection between the blade 420 and the surface 425 is substantially continuous when the cutting board 422 is drawn up against the blade 420.

The cutter assembly 403 may comprise a sharp blade 421 located at the distal end 423 of a catheter 401, and further comprise a cutting board 422 disposed distal to the sharp blade 421, said assembly 403 being designed so that leaflet tissue LF may be maneuvered into a space between the blade 421 and the cutting board 422, and by moving the cutting board 422 or the blade 421, the tissue LF may be cut by the blade 421.

In another embodiment, the catheter 401 of FIG. 27 may comprise a cutter assembly 430 configured for both separating the fixation device 14 from the leaflets LF and removing the fixation device 14 from the heart. The catheter 400 may be associated with a stapler assembly 431 for affixing the leaflets LF before, after, or while the fixation device 14 is separated from them. For example, the leaflets may be stapled or otherwise joined together prior to removal of the fixation device 14, particularly where portions of leaflets LF are removed with device 14.

As shown in FIG. 30A, the catheter 401 may comprise a cutter assembly 430 having a distal end 423 which comprises an annular blade 432. After being advanced out of the outer guide catheter 405, the catheter 401 is pushed around the fixation device 14 from below. The annular blade 432 will cut the tissue LF to which the fixation device 14 is attached in order to at least partially separate the fixation device 14 from the tissue it is connected to. The annular blade 432 may function similar to an apple corer, as it punches into the tissue LF surrounding the fixation device 14.

The cutter assembly 430 may further comprise a grabbing mechanism 433 located within the lumen 434 of the catheter 401. The grabbing mechanism 433 is slidably movable within the lumen 434, and can be slidably moved toward and away from the distal end 423 of the catheter 401.

The grabbing mechanism 433 may comprise a stationary arm 435 and a moveable arm 436. The grabbing mechanism 433 may further comprise an elongate member 437 that runs the length of the catheter 401 and connects to the moveable arm 436. The elongate member 437 may be used to manipulate the moveable arm 436 from the proximal end of the catheter 401. By moving the moveable arm 436 closer to the stationary arm 435, grabbing mechanism 433 may be placed in a closed position, and by moving the moveable arm 436 away from the stationary arm 435, the grabbing mechanism 433 may be placed in an open position. The elongate member 437 may also permit the slidable movement of the grabbing mechanism 433. In other embodiments, both arms 435 and 436 may be moveable. The grabbing mechanism 433 may function similar to tweezers. By applying force to one or both sides of the fixation device 14, the grabbing mechanism 433 may stabilize the fixation device 14, serve as a retaining means for retaining the device 14 in the control of the person manipulating the catheter 401, and assist with the removal of the device 14 from the patient.

The grabbing mechanism 433 may be used to help hold the fixation device 14 and any immediately surrounding tissue in the catheter 401. Once the fixation device 14 is separated from the heart, it may then be removed from the heart.

The grabbing mechanism used in the cutter assembly 430 may instead comprise a lasso-type capturing mechanism 408, as described above in reference to FIG. 28, or any other type of capturing mechanism. It may be preferable, if a lasso-type capturing mechanism 408 is used with the cutter assembly 430, for the cutter assembly 430 to approach the fixation device 14 from the ventricle side of the heart.

The lasso-type capturing mechanism 408 could be advanced from within the catheter 401, and used to firmly hold onto the fixation device 14. Then the catheter 401 could be advanced toward the fixation device 14 so that the annular blade 432 cuts the fixation device 14 out of the leaflet tissue. The cutter assembly 430 could then be withdrawn from the heart with the fixation device 14. As described herein, the leaflets may be stapled or otherwise joined together at a location adjacent to fixation device 14 prior to removal of device 14, particularly where some leaflet tissue surrounding device 14 is removed with device 14. This prevents formation of an unwanted hole or holes within the mitral valve where device 14 once resided, as a result of removal of device 14 with a small amount of surrounding leaflet tissue. This may be helpful, so as to prevent such a hole from preventing desired closing of the mitral valve during its normal operation.

In another embodiment, the cutter assembly 430 may use as its cutting means radiofrequency energy, laser energy, a rotating tip or other cutter as its cutting mechanism, instead of or in addition to the annular blade shown in FIG. 30A. Additional or alternative grabbing mechanisms 433 may also be used as retaining means. For example, the grabbing mechanism may be replaced by a vacuum mechanism or a lasso-type capturing mechanism.

The cutter assembly 430 may approach the fixation device 14 from the left atrium LA, or may approach the fixation device 14 from the left ventricle LV. In some embodiments, as depicted schematically in FIGS. 30B-30C, the cutter assembly 430 may be configured and/or maneuvered so that the annular blade 432 is advanced between the distal elements 18 and proximal elements 16 of the fixation device 14. This may serve to separate the proximal elements 16 from the leaflet tissue LF.

Figure 30C:
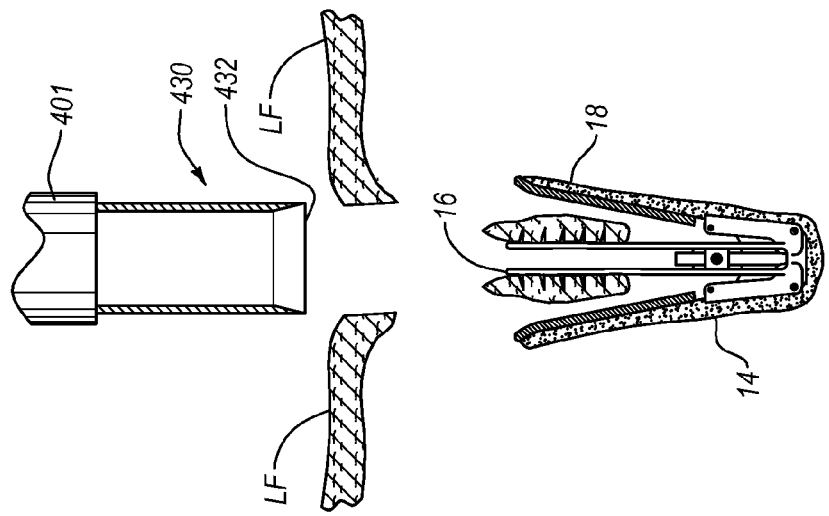
Figure 30B:
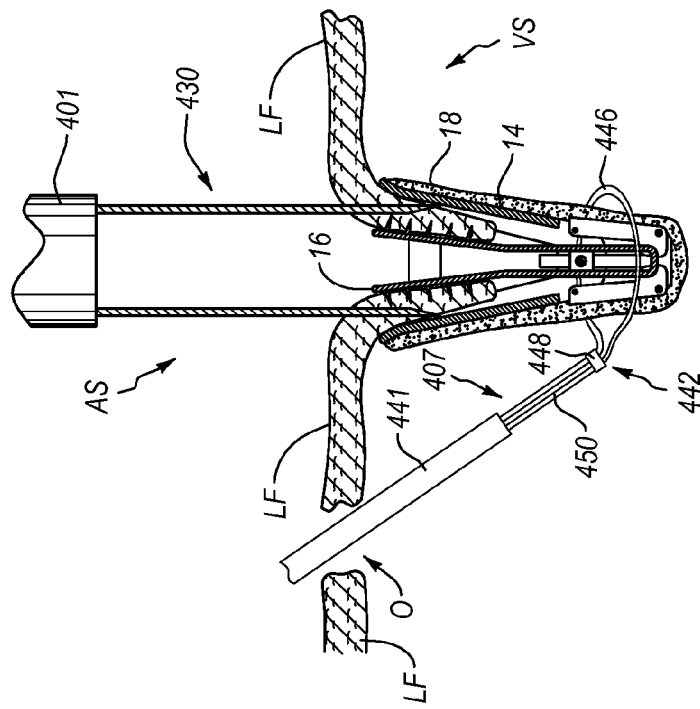

FIGS. 30B-30C show progressive cross sectional views of the cutter assembly 430 cutting the leaflet tissue LF in this way. Because the proximal elements 16 may be designed to help grip the leaflet tissue LF, cutting between the distal elements 18 and proximal elements 16 of the fixation device 14 may reduce damage to other portions of the leaflet tissue LF by allowing the fixation device 14 to be pulled away from the mitral valve MV without needing to cut the entire fixation device 14 out of the mitral valve MV.

Before, while, or after the cutter assembly 430 cuts or separates the leaflets LF from the fixation device 14, a grabbing mechanism 433 or a capturing mechanism 407 associated with a separate catheter 441 may be placed in close proximity to the fixation device on either the atrial side AS or ventricle side VS of the mitral valve MV. The grabbing mechanism 433 or capturing mechanism 407 may be associated with a separate catheter 441.

As illustrated in FIG. 30B, one method for placing the grabbing mechanism 433 or capturing mechanism 407 in close proximity to the fixation device on the ventricle side VS may involve placing the catheter 441 and the grabbing mechanism 433 or the capturing mechanism 407 (or just the grabbing mechanism 433 or the capturing mechanism 407) from the atrial side AS of the mitral valve MV and through an orifice of the mitral valve MV to reach the fixation device 14 from the ventricle side VS. Preferably, this is done prior to removal of the clip, while there are two orifices of the mitral valve MV.

As shown in FIG. 30B, the capturing mechanism 407 comprises a type of snare or lasso structure 442 that may comprise a loop 446, a connection or cinch point 448, and an arm 450.

Once the proximal elements 16 are separated from the leaflets LF, the grabbing mechanism 433 or capturing mechanism 407 associated with a separate catheter 441 may be used to pull the fixation device 14 apart from the mitral valve MV. Or, after the fixation device 14 is cut apart from or otherwise separated from the leaflets LF, the grabbing mechanism 433 or a capturing mechanism 407 associated with a separate catheter 441 may be used to pull the fixation device 14 apart from the mitral valve MV.

Figure 30E:
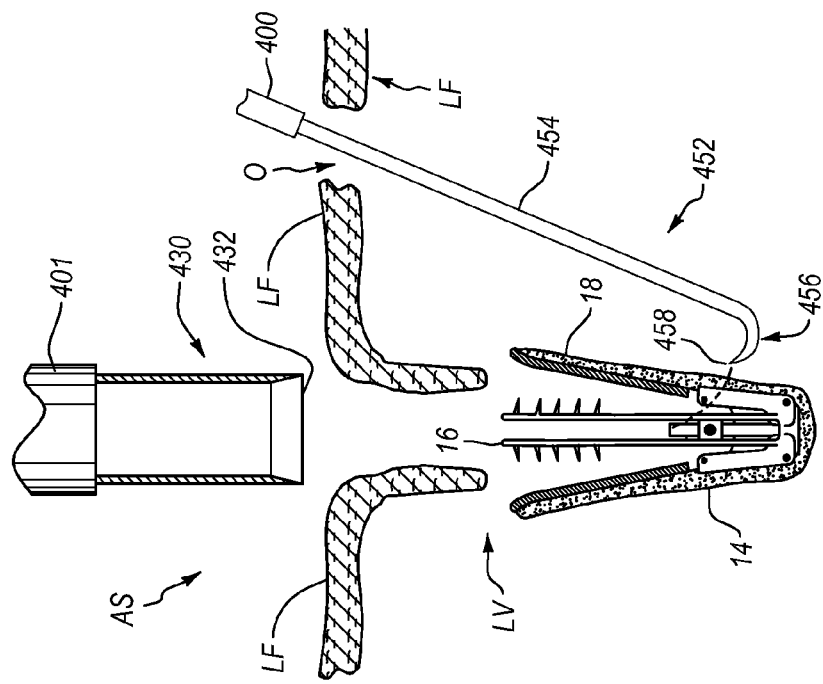
FIGS. 30D-30E illustrate another exemplary method of removing a fixation device and an exemplary method of unlocking the harness.
Figure 30D:
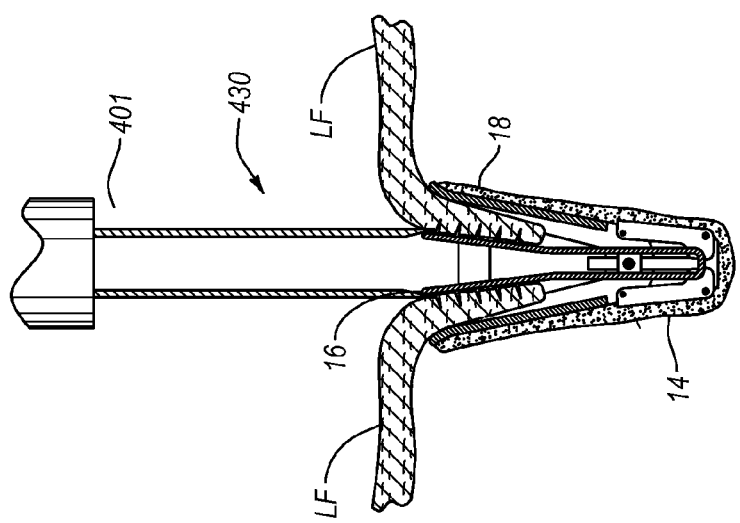

FIGS. 30D-30E show progressive cross sectional views of the cutter assembly 430 removing the fixation device 14 from the leaflet tissue LF shortly after implantation of device 14 and before extensive tissue in-growth has occurred. Before extensive tissue in-growth has occurred, it may be possible to separate the proximal elements 16 from the leaflet tissue LF without needing to cut the leaflet tissue LF. This method may reduce damage to the leaflet tissue LF by allowing the fixation device 14 to be pulled away from the mitral valve MV without needing to cut leaflet tissue LF surrounding the fixation device 14. For example, cutter assembly may be advanced between the leaflet tissue LF and proximal elements 16, and manipulated to work leaflet tissue LF away from proximal elements 16. Once the proximal elements 16 are separated from the leaflets LF, the grabbing mechanism 433 or a capturing mechanism 407 associated with a separate catheter may be used to carefully pull the fixation device 14 apart from the leaflets LF of mitral valve MV. Other devices than the cutter assembly 430 may also be used to separate the proximal elements 16 from the leaflet tissue LF in this method.

FIG. 30E additionally shows an unlocking device 452 which may be used to unlock the release harness 108 of the fixation device 14. The unlocking device 452 may be advanced into the left ventricle LV from the atrial side AS of the heart, through an orifice O. The unlocking device 452 may be associated with catheter 400. The unlocking device 452 may comprise an elongate body 454 and a hook 456 with a tip 458. The tip 458 of the hook 456 may be manipulated to unlock the release harness 108. The release harness 108 is preferably radiopaque and the hook 456 is also preferably radiopaque, so that they may be viewed via x-ray or other imaging technique. It may also be possible to view the release harness 108 and hook 456 through an echocardiogram.

Figure 31:
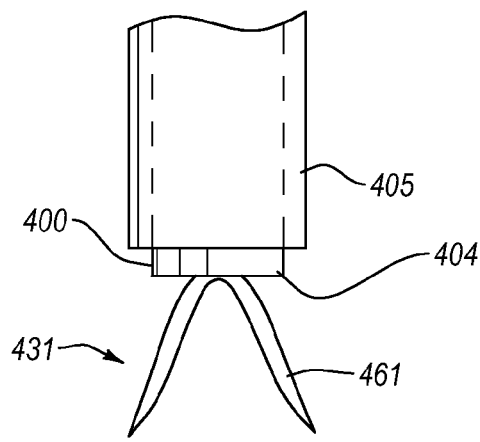
FIG. 31 illustrates an embodiment of a stapler assembly to be used in association with the removal and/or disabling of a fixation device.

The cutter assembly 430 may further comprise a catheter 400 including a stapler assembly 431 for affixing the leaflets LF. As depicted in FIG. 31, the stapler assembly 431 is located at the distal end 404 of the catheter 400.

The stapler assembly 431 may provide a means for installing a staple 461 into each leaflet LF before, after, or while the fixation device 14 is removed. One staple 461 may be used for the anterior mitral valve MV leaflet LF, and another staple 461 for the posterior mitral valve MV leaflet LF, if both leaflets LF are cut. Each staple 461 upon deployment may serve to pull together the part of a leaflet LF where the fixation device 14 was cut out or is going to be cut out. In another embodiment, a staple may hold both leaflets LF together, if desired.

Figure 35:
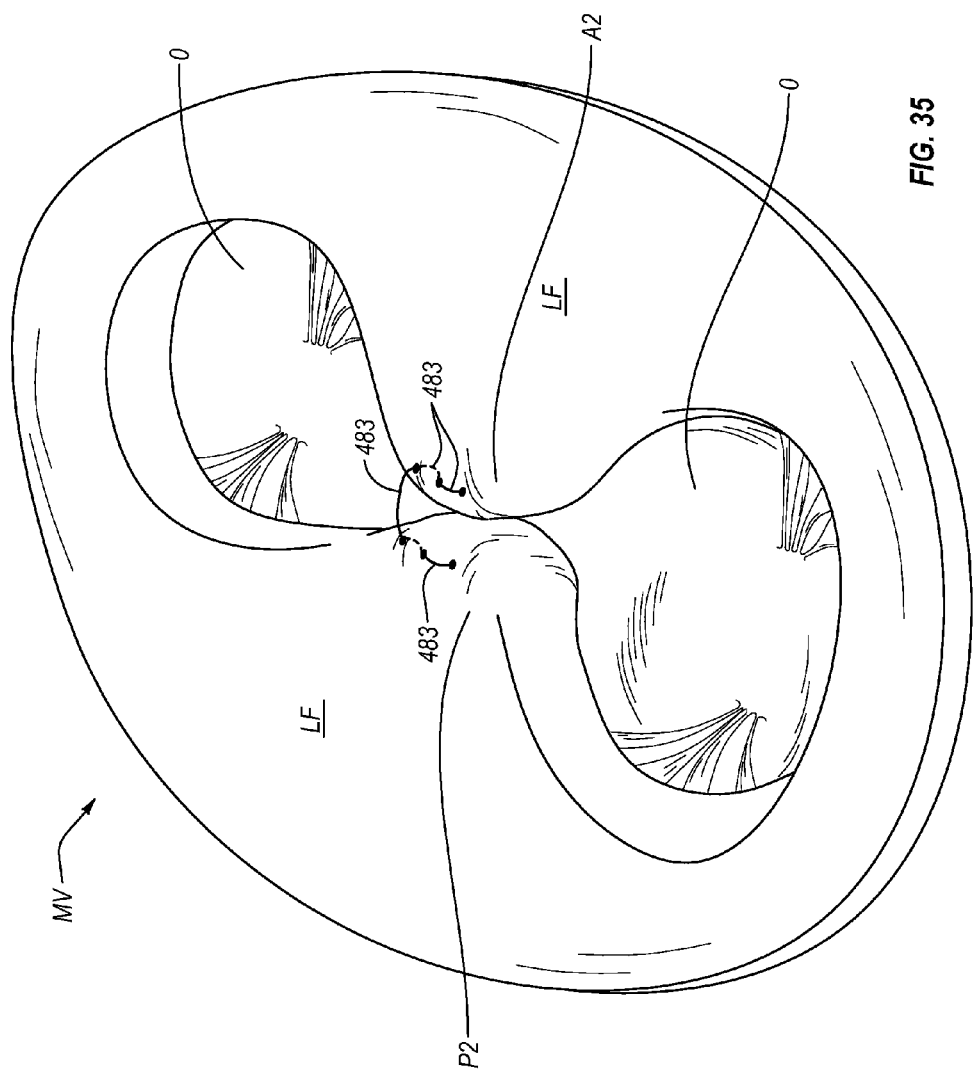
FIG. 35 illustrates a sutured mitral valve.

The leaflets may be stapled or otherwise joined together prior to or simultaneous with removal of the fixation device 14, particularly where portions of leaflets LF are removed with device 14. For example, the leaflets may be stapled or otherwise joined together at a location adjacent to fixation device 14 prior to removal of device 14, particularly where some leaflet tissue surrounding device 14 is removed with device 14. This prevents formation of an unwanted hole within the mitral valve where device 14 once resided, as a result of removal of device 14 with a small amount of surrounding leaflet tissue. This may be helpful, so as to prevent such a hole from preventing desired closing of the mitral valve during its normal operation. Any joining mechanism may be employed (e.g., staple, of fastener, sutures, etc.). For example, FIG. 35 illustrates a suture purse-string type joining of the opposed leaflets LF. Such a purse-string technique and mechanism could be used prior to or simultaneous with removal of device 14, so as to prevent a hole from being present where leaflet tissue is removed with device 14.

The catheter 400 holds a staple 461 in a position in which it can be installed into a mitral valve MV leaflet LF. By controlling the proximal end of the catheter 400, the staple 461 is directed to a leaflet LF and pushed into the leaflet. The catheter 400 releases the staple 461 after it is installed in a leaflet LF.

Figure 32A:
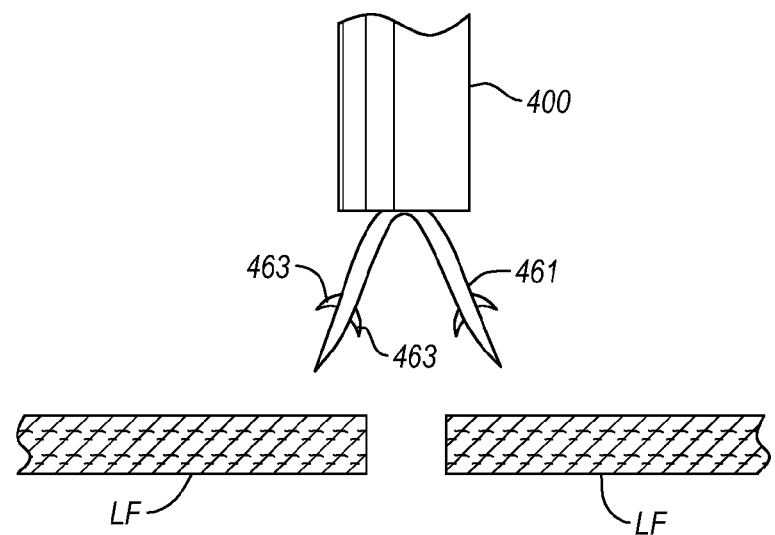
FIGS. 32A-32B illustrate an exemplary method by which a staple may be affixed to leaflet tissue.
Figure 32B:
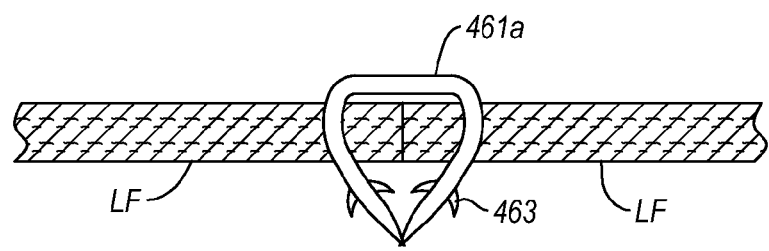

Each staple 461 may be made of a shape-memory alloy such as Nitinol. FIGS. 32A-32B schematically illustrate the use of such a staple 461. The staple 461 may be V-shaped when initially inserted into mitral valve MV tissue LF. Then as the staple 461 comes to body temperature, it may then become U-shaped (461a), e.g., a closed U-shape, pulling together the mitral valve MV tissue LF. In another embodiment, the staple 461 may be a shape-memory material that assumes a J-shape as it comes to body temperature. The staple 461a may pull the tissue together, or the tissue may first be pulled together by another device and then stapled. It will be appreciated that staples with different configurations may also support repair of the tissue. Each staple 461 may also be biodegradable or bioabsorbable, or made of any suitable material, such as a polymer. The staple or staples 461 may also serve to join the two leaflets LF together. This may approximate the position the leaflets LF were in when the fixation device 14 was installed.

The staple or staples 461 may be installed into the leaflet or leaflets LF in an un-deployed state prior to the removal of the fixation device 14 and then assume or be made to assume a deployed state after the fixation device 14 is removed.

As shown in FIGS. 32A and 32B, it may be preferable to have a barb or barbs 463 at the ends or along the edges or sides of the staples which are inserted into tissue. This may permit the staples 461 to affix more stably or irreversibly to the leaflet tissue LF. Instead of passing all of the way through the leaflet tissue LF, as depicted in FIG. 32B, a staple 461 may be placed only partially through the tissue. In another embodiment, it may be preferable to have the staple 461 designed so that they can be removed from the leaflet tissue LF easily during installation and re-positioned as necessary.

The staple means at a distal end of catheter 400 may comprise a staple 461 detachably retained on a distal end 404 of a catheter 400, wherein said staple 461 is configured to pull or hold damaged tissue together in a position that approximates a healed tissue configuration.

In one embodiment, the staple 461 may be installed by a device such as or similar to a surgical tissue stapler. In another embodiment, the staple 461 may be installed using an anvil held by a separate catheter. The staple 461 may be pressed against the anvil to assume the desired closed staple configuration. Straight, curved, or circular staples may be used, for example. The stapler may comprise a knife to both assist with removal of the fixation device 14 and affix the tissue LF after cutting. Such staples 491 may be made of any suitable substance, such as titanium or nitinol, and may even be bioabsorbable. In addition to staples 461, clips may also be used.

In other embodiments, other methods or means for repairing the leaflets LF may include, but are not limited to, thermal energy, purse string suturing, purse string suturing anchored with barbs, staples, sutures or wire, cinching of barbs, sutures, or wires, etc. Either or both of catheters 400 and 401 may be associated with devices capable of performing any of these methods.

Figure 33:
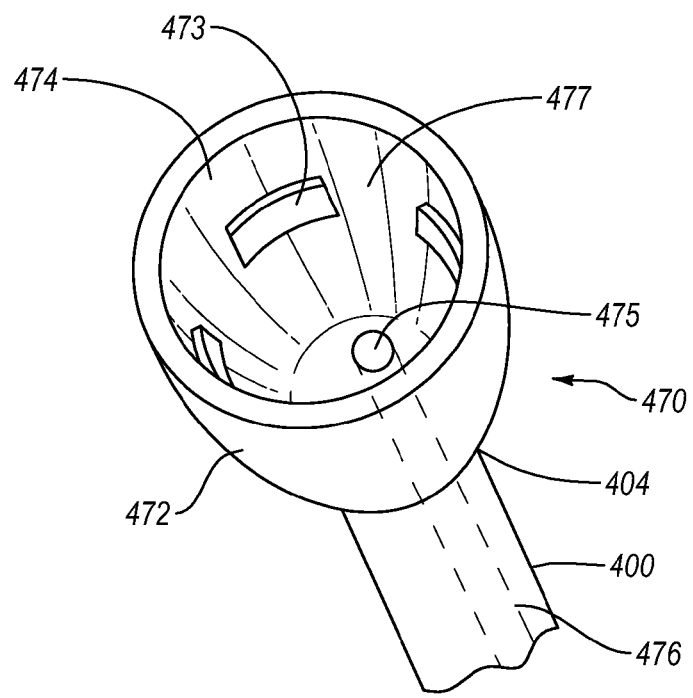
FIG. 33 illustrates an embodiment of a cone assembly.
Figure 34:
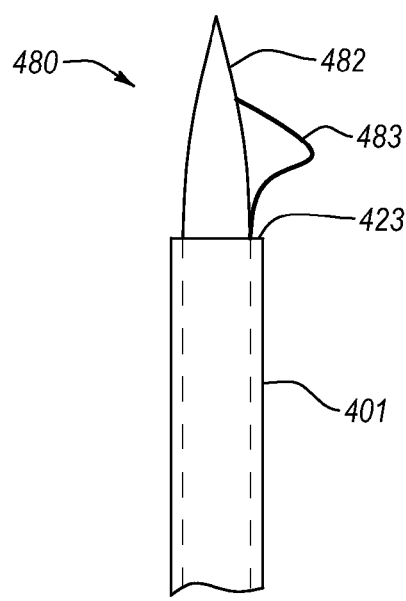
FIG. 34 illustrates an embodiment of a suture assembly.

In another embodiment, the catheter 400 of FIG. 27 may be associated with a cone assembly 470 and the catheter 401 may be associated with a suture assembly 480, as shown in FIGS. 33-34.

The cone assembly 470 may comprise a balloon 472 in the shape of a hollow cone that is located on the distal end 404 of the catheter 400.

More particularly, the balloon 472 may be shaped like a hollow cone with its apex cut off (that is, a hollow truncated cone or frustum). For example, as shown in FIG. 33, the balloon 472 is oriented such that the apex of the cone (if it had an apex) would face toward the proximal end of the catheter 400. FIG. 33 shows the balloon inflated. Such a cone structure may be particularly well-suited to the functions of the present methods, although other structures may also be used.

Preferably the balloon 472 is advanced into the left ventricle LV of the heart in a deflated condition. Once it is positioned, for example, beneath the fixation device 14 in the left ventricle LV, the balloon 472 is inflated. Techniques for the inflation of balloons located on catheters are known in the art. For example, the balloon 472 may be inflated with inflation material such as water, saline, or a gas. In one embodiment, the balloon 472 is configured so that the entire fixation device 14, as well as any tissue growing around the distal elements of the fixation device 14, can fit within the cavity 477 created by the balloon 472.

As illustrated in FIG. 33, heating elements 473 may be located on the interior surface 474 of the balloon 472. The heating elements 473 may be intermittently spaced or form a continuous strip of heating elements 473 within the interior periphery of the balloon 472, or be placed in a variety of patterns or arrangements on the interior surface 474 of the balloon 472. The heating elements 473 may be configured so that heat can be selectively applied to the tissue around the fixation device 14. The balloon 472 may also be lined with radiofrequency elements or similar energy delivery elements. In another embodiment, the hollow conical structure may be a solid structure rather than a balloon.

Preferably, the device is designed so that the heating elements 473 can be selectively turned on, off, and otherwise controlled from the handle at the proximal end of the catheter 400. The heat energy may be used to separate the leaflet tissue LF from the fixation device 14. The heat energy may be applied to a portion of leaflet tissue LF distal to the free ends 54 of the distal elements 18 of the fixation device 14 (e.g., just beyond the edge of distal elements 18).

The cone assembly 470 may be configured to deliver other forms of energy in addition to or instead of heat energy, such as radiofrequency energy, laser, etc., for the purpose of separating the leaflet tissue LF from the fixation device 14. The heat or other energy may also be used to fuse or partially fuse the leaflet tissue LF together to repair it. If thermal energy is used to repair the leaflets LF, a vice or jaw may be used to secure the damaged portions of a leaflet to each other prior to thermal fusing. The heat or other energy could also be used to fuse the two leaflets to each other. For example, it may be desirable to fuse the two leaflets together in a position approximating their configuration when fixation device 14 was installed (e.g., similar to purse-string suturing of leaflets LF in FIG. 35). It may be possible for heat or other energy to be applied to the tissue and have that energy serve to cut the leaflet tissue LF in such a way that the fixation device 14 can be removed from the tissue LF. Such energy employed for cutting may at the same time cauterized and seal the tissue. The cone assembly 470 is another example of cutting means.

If the cone assembly 470 is used to separate both leaflets LF from the fixation device 14—as opposed to separating one leaflet LF, and thereby disabling the fixation device 14—the fixation device 14 may then be removed from the heart. The balloon 472 may be deflated around the fixation device 14 prior to removal of the cone assembly 470 and the fixation device 14. As such, the cone assembly may also be an example of retaining means. Alternatively, a sheath (not pictured) may be advanced over the balloon 472 to capture the fixation device 14. The fixation device 14 may also be captured into a conduit or expandable basket (not pictured).

The cone assembly 470 may further include a vacuum mechanism 475. The vacuum mechanism 475 may comprise a tube or lumen 476 within the catheter 400 as depicted in FIG. 33. A suction or other vacuum device (not pictured) may be connected at the proximal end of the catheter (not pictured), for example, at the handle 304, to apply a suction force at the proximal end of the tube or lumen 476 of the vacuum mechanism 475. This suction force may be translated along the length of the tube or lumen 476 to help hold the separated fixation device 14 in the balloon 472. This may be useful, for example, to permit the fixation device 14 to be withdrawn out of a side access point in the heart, as it may help prevent the fixation device 14 from falling out of the balloon 472. In uses where the fixation device 14 is made from a magnetic material, a magnet in the cone assembly 430 may also perform this function. The cone assembly 470 may also include any of the other retaining means described herein, and the cone assembly 470 may be itself considered a retaining means.

The cone assembly 470 may comprise a device configured to remove a fixation device 14 by the selective application of thermal, electrical, or other types of energy to leaflet tissue LF located near the fixation device 14. It may further comprise a retaining means for ensuring that the fixation device 14 is retained within the cone assembly 470 for removal from the heart, such as a vacuum mechanism 475.

The system may further comprise a catheter 401 associated with a suture assembly 480 for affixing the leaflets LF. As depicted in FIG. 34, the suture assembly 480 may be disposed at the distal end 423 of the catheter 401.

Suture assembly 480 may comprise a needle 482 and a thread, cord, or wire 483. The suture assembly 480 may also comprise sutures with barbs. Such a suture assembly 480 may serve to close or otherwise repair a cut on leaflet(s) LF after fixation device 14 has been removed. As described above, such suturing or other joining of leaflets LF may be performed prior to or simultaneous with removal of device 14.

Even after the fixation device 14 is removed, it may be desired to maintain the mitral valve MV structure in a double-orifice configuration (e.g., similar to that shown in FIG. 4). Therefore, the present methods may include suturing (e.g., using suture assembly 480) to suture leaflets LF. In an embodiment, leaflets may be purse-string sutured, as pictured in FIG. 35. In such a method, the A2 region of the mitral valve MV is sutured to the P2 region. Before, after, or while the fixation device 14 is cut out of the mitral valve MV, a suture assembly (e.g., assembly 480) may be used to suture the two leaflets LF to each other. This suturing may maintain the leaflets in (or return the leaflets to) approximately the same arrangement they were in prior to the fixation device 14 being removed. The suture thread, cord, or wire 483 could be sewn into one leaflet LF and then the other, and then pulled taut like a purse string. A suture assembly may also be used to suture each leaflet LF separately, to assist the leaflets LF in healing or prepare them for further procedures to be performed. It may be preferable to place the sutures prior to removal of the fixation device 14, and draw them taut after the fixation device 14 is removed.

Anchoring for the purse string sutures may be achieved by using a suture anchor, barbs, staples, additional sutures, wire, etc. Alternatively, the leaflet(s) LF may be repaired by using cinching of barbs, sutures, anchors with eyelets, or wires. For example, hooked barbs may be installed on one leaflet LF, while a corresponding barb with an eye may be installed on the other leaflet. The hook of the hooked barb on one leaflet may be engaged with the eye of the barb on the other leaflet to hold both leaflets LF of the mitral valve MV together. It may be preferable to affix the sutures, barbs, staples, wires, etc. or other mechanism for attaching opposed leaflets LF prior to removal of the fixation device 14. For example, it may be easier to secure the leaflets to one another prior to removal of device 14, as device 14 serves to anchor and hold leaflets adjacent one another. In addition, particularly where any leaflet tissue LF is removed with device 14, it may be preferred to secure the leaflets to one another at a location adjacent to device 14 (e.g., by staple, suture, etc.) so as to prevent formation of a hole that would resist closure during the systolic portion of the cardiac cycle where device 14 and removed leaflet tissue LF once was. In one embodiment, it may be desired to place needles or hooks into the tissue LF before the leaflet device before the fixation device 14 is removed, and then draw the needles or hooks through the tissue to bring the leaflets LF together or repair each leaflet LF separately.

Figure 36:
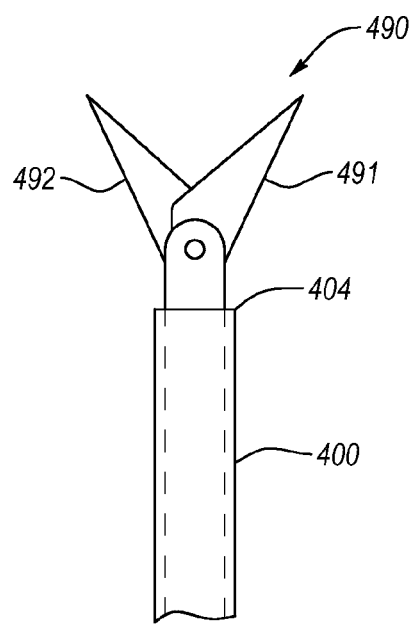
FIG. 36 illustrates another cutting assembly.

In another embodiment, the catheter 400 of FIG. 27 may be associated with a cutter assembly 490. As illustrated in FIG. 36, the cutter assembly 490 may be located at the distal end 404 of the catheter 400. The cutter assembly 490 may comprise a pair of arms 491 and 492. At least one of the arms 490 and 491 may be capable of being moved in a scissor-like fashion and capable of being controlled from the proximal end of the catheter 400 (e.g., at a handle). The moveable arms 491 and 492 may be controlled to close around a fixation device 14 and cut the fixation device 14 into approximately two pieces. One portion of the fixation device 14 (e.g., including a set of one proximal element 16 and one distal element 18) may remain with one leaflet LF of the mitral valve MV while the remaining portion of the fixation device 14 (e.g., including a set of one proximal element 16 and one distal element 18) may remain with the other leaflet LF of the mitral valve MV. The cutter assembly 490 may use mechanical force, heat, radiofrequency energy, or any other suitable cutting mechanism to partition the fixation device into two or more portions, separating the leaflets of the mitral valve. Catheter 400 may further include an enclosure (not pictured) or other stabilizing mechanism to hold the parts of the fixation device 14 while the device is being cut.

The moveable arms 491 and 492 may also be closed around a leaflet LF adjacent to the free end 54 of one of the distal elements 18 of the fixation device 14 in order to separate that mitral valve leaflet LF from its corresponding distal element 18. Such a method may leave the device 14 attached to only one of the leaflets. The cutter assembly 490 may also be used to separate both leaflets LF from the fixation device 14, after which the device may be removed from the body.

As with the other procedures described herein, this may be done in preparation for further procedures being performed on the mitral valve MV, such as mitral valve annuloplasty, balloon valvuloplasty, mitral valve repair, or installation of a replacement valve.

The cutter assembly 490 may further comprise thermal, electric, or other elements used to cauterize the leaflet tissue LF (e.g., to cut and cauterize substantially simultaneously). The cutter assembly 490 may be configured that, at the same time heat or other energy is used to separate a leaflet LF from the fixation device 14, the heat cauterizes or fuses the tissue to repair it.

The cutting mechanism associated with the cutter assembly 490 may be particularly configured for cutting leaflet tissue LF or the fixation device 14. For example, the Abbott Vascular MitraClip® fixation device is formed of a cobalt-chromium alloy, is covered with polyester, and may include a nitinol component, so a cutting tool sufficient to cut through one or more of those materials may be provided to remove a MitraClip® fixation device. Where the cutter assembly 490 is merely used for cutting leaflet tissue, the materials and/or specifications of the cutter assembly 490 may be different.

After a fixation device 14 is installed in the heart, tissue typically grows around the device. Cutting the fixation device 14 into two parts may be done even when the fixation device 14 is fully in-grown, or if the device is only partially in-grown, or not in-grown to any significant degree. If the fixation device 14 is to be left in the heart after it is cut (e.g., partitioning it into two portions, one remaining with each leaflet), it may be preferable to ensure that the fixation device 14 is fully or substantially fully in-grown prior to cutting.

B. Improved Fixation Device with a More Easily Accessible Harness

As shown and described in conjunction with FIGS. 16-19, the implanted fixation device 14 may have a release harness 108 which can be used to release the locking mechanism 106. When the locking mechanism 106 is released, the fixation device 14 may be more easily removed. The present systems may include a catheter-based device used to activate (e.g., unlock) the release harness 108, such as a catheter with a hook, lock lines, or other engagement structure on its distal end that can engage release harness 108, such as hook 456.

In many circumstances, tissue may have grown around the fixation device 14, and the release harness 108 may no longer be readily accessible to interventional tools. As such, according to one embodiment, an improved fixation device 14 is provided. Such an improved device 14 may include features making it easier to access release harness 108 and release the locking mechanism 106 on of the fixation device 14 in the process of removing it after it has been installed in a heart.

Figure 37:
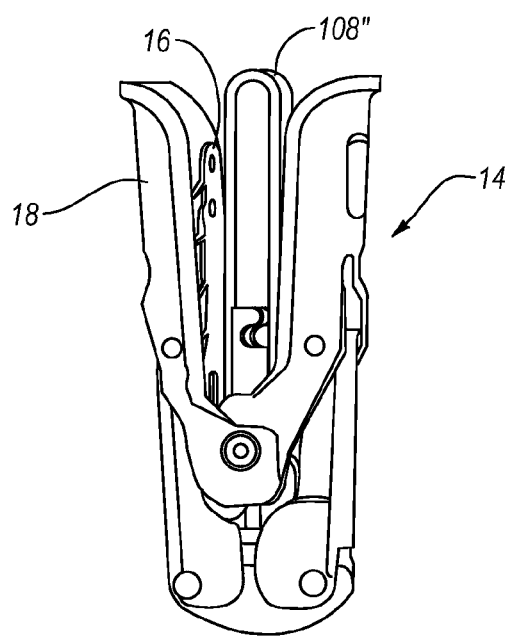
FIG. 37 illustrates an improved fixation device similar to that of FIG. 14, but with an elongated release harness.

For example, the fixation device 14 release harness 108 may be extended in length to increase the accessibility of the release harness. If the release harness 108 were longer, for example, as the release harness 108" shown in device 14 of FIG. 37, then a hook or other engagement device on a catheter, such as hook 456, advanced into the heart from the atrial or ventricular side may be able to more easily unlock the fixation device 14 using the release harness 108" even after tissue has grown up around much or substantially all of the fixation device 14. For example, as illustrated in FIG. 37, the release harness 108" may extend beyond the free ends of the proximal elements 16, distal elements 18, or both when the device is in a closed and locked position, as shown.

Unlocking the fixation device 14 may allow for the proximal elements 16 and distal elements 18 to be more easily removed from the leaflets LF and for the device 14 to be more easily removed from the heart. With the fixation device 14 unlocked, a catheter with a retaining means and/or a catheter with a cutting means may be used to pull or push the distal elements 18 away from the leaflets LF. It may be necessary to stabilize the fixation device from the opposite (e.g., ventricle) side prior to accessing the release harness 108. It may only be possible to remove the fixation device 14 by unlocking the harness 108 prior to extensive tissue in-growth occurring around the device. For example, this method may be particularly helpful within about 7 days, 15 days, 30 days, or 60 days after implantation of the fixation device. As the rate of tissue growth may vary in individuals based on a variety of factors, and tissue is radiolucent, it may not be possible to know whether tissue growth is too extensive for the release harness 108 to be unlocked without attempting to unlock it.

In another embodiment, an improvement to the fixation device 14 may be to make it biodegradable while still serving to secure the leaflets together, so that if, for example, a replacement valve is later installed, the fixation device 14 may have biodegraded and only the leaflets LF will need to be separated (e.g., grown together as the device 14 biodegrades).

In another embodiment, it may be preferable to implant a replacement valve in each of the orifices using the fixation device as an anchor. A device comprising two replacement valves and shaped approximately like a figure-eight may be so installed. This may be desirable if mitral regurgitation reduction is insufficient and the fixation device 14 cannot be removed or its removal would otherwise be undesirable. Such replacement valve devices, systems, and methods are disclosed in U.S. application Ser. No. 14/216,813, herein incorporated by reference in its entirety.

C. Double Orifice Balloon Valvuloplasty

In some circumstances, such as when mitral valve stenosis occurs after the implantation of a fixation device 14, and the fixation device is not able to be removed, or removal is otherwise undesirable, balloon valvuloplasty may be performed in both orifices. This valvuloplasty may be performed in both orifices simultaneously or in one orifice first and then in the other orifice. It may be possible to anchor a device for performing the balloon valvuloplasty to the fixation device 14. Performing balloon valvuloplasty in both orifices simultaneously or nearly simultaneously may support the procedure.

Figure 38:
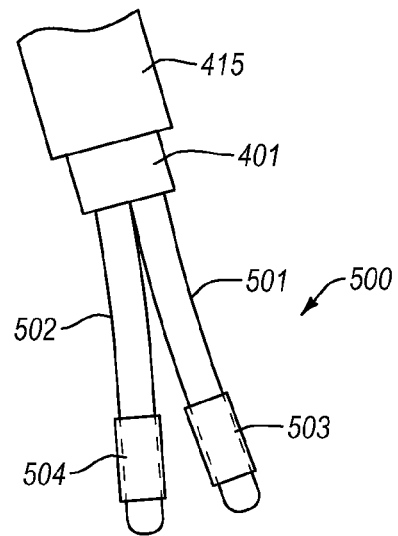
FIG. 38 illustrates a double orifice balloon valvuloplasty device.

For example, as illustrated in FIG. 38, a catheter 401 may be associated with a double balloon valvuloplasty assembly 500. The balloon valvuloplasty assembly 500 may comprise two arms 501 and 502 which are configured so that, once the balloon valvuloplasty assembly 500 is advanced out of the outer guide catheter 415, the two arms 501 and 502 separate at an appropriate distance so that one arm 501 can be advanced into one orifice of the mitral valve double orifice structure formed by a fixation device 14 and the other arm 502 can be advanced into the other orifice (e.g., FIGS. 4 and 35 show the two orifices O). Arms 501 and 502 each have a balloon 503 and 504 disposed at or near a distal end of each respective arm. Balloons 503 and 504 can be inflated when the arms 501 and 502 are advanced to a position within the orifices O. The inflation of the balloons 503 and 504 may be done by methods known in the art, and can be controlled by a handle located at the proximal end of the outer guide catheter 415.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method of disabling a fixation device that holds anterior and posterior leaflets of the mitral valve together, the fixation device comprising a clip and being deployable during a first procedure, the method comprising:
    during a second procedure, cutting the previously deployed fixation device so that an anterior distal element and an anterior gripping element of the fixation device, which hold the anterior leaflet therebetween, remain attached to the anterior leaflet, and a posterior distal element and a posterior gripping element of the fixation device, which hold the posterior leaflet therebetween, remain attached to the posterior leaflet, cutting the previously deployed fixation device separates the anterior and posterior leaflets.

2. The method of claim 1, the method further comprising performing a procedure selected from the group consisting of mitral valve annuloplasty, balloon valvuloplasty, mitral valve repair, installation of a replacement valve, and combinations thereof.

3. The method of claim 1, the method further comprising repairing a damaged leaflet or damaged leaflets by affixing the leaflet or leaflets together.

4. A method of removing a fixation device that holds anterior and posterior leaflets of the mitral valve together, the fixation device comprising a clip and being deployable during a first endovascular procedure, the method comprising:
    accessing the fixation device holding the anterior and posterior leaflets of the mitral valve together through a second endovascular procedure that advances a tool through the vasculature of a patient and into the heart;
    cutting the fixation device with the tool so that an anterior distal element and an anterior gripping element of the fixation device, which hold the anterior leaflet therebetween, remain attached to the anterior leaflet, and a posterior distal element and a posterior gripping element of the fixation device, which hold the posterior leaflet therebetween, remain attached to the posterior leaflet, cutting the previously deployed fixation device separates the anterior and posterior leaflets.

5. The method of claim 4, the method further comprising performing a procedure selected from the group consisting of mitral valve annuloplasty, balloon valvuloplasty, mitral valve repair, installation of a replacement valve, and combinations thereof.

6. The method of claim 4, the method further comprising repairing a damaged leaflet or damaged leaflets by affixing the leaflet or leaflets together.

* * * * *